(12) United States Patent
Clawson

(10) Patent No.: US 8,355,483 B2
(45) Date of Patent: Jan. 15, 2013

(54) STROKE DIAGNOSTIC AND INTERVENTION TOOL FOR EMERGENCY DISPATCH

(76) Inventor: Jeffrey J. Clawson, Salt Lake City, UT (US)

( * ) Notice: Subject to any disclaimer, the term of this patent is extended or adjusted under 35 U.S.C. 154(b) by 507 days.

(21) Appl. No.: 12/558,045

(22) Filed: Sep. 11, 2009

(65) Prior Publication Data

US 2011/0064204 A1  Mar. 17, 2011

(51) Int. Cl.
*H04M 11/04* (2006.01)
(52) U.S. Cl. ....... 379/45; 379/38; 379/265.01; 600/300; 128/904; 128/905; 707/2
(58) Field of Classification Search .............. 379/45, 379/265.01, 38; 600/300; 128/903, 904, 128/905; 705/2
See application file for complete search history.

(56) References Cited

U.S. PATENT DOCUMENTS

| | | | |
|---|---|---|---|
| 3,799,147 A | 3/1974 | Adolph et al. |
| 4,130,881 A | 12/1978 | Haessler et al. |
| 4,164,320 A | 8/1979 | Irazoqui et al. |
| 4,237,344 A | 12/1980 | Moore |
| 4,290,114 A | 9/1981 | Sinay |
| 4,338,493 A | 7/1982 | Stenhuis et al. |
| 4,360,345 A | 11/1982 | Hon |
| 4,455,548 A | 6/1984 | Burnett |
| 4,489,387 A | 12/1984 | Lamb et al. |
| 4,731,725 A | 3/1988 | Suto et al. |
| 4,839,822 A | 6/1989 | Dormond et al. |
| 4,858,121 A | 8/1989 | Barber et al. |
| 4,865,549 A | 9/1989 | Sonsteby |
| 4,922,514 A | 5/1990 | Bergeron et al. |
| 4,926,495 A | 5/1990 | Comroe et al. |
| 4,945,476 A | 7/1990 | Bodick et al. |
| 4,967,754 A | 11/1990 | Rossi |
| 5,063,522 A | 11/1991 | Winters |
| 5,065,315 A | 11/1991 | Garcia |
| 5,072,383 A | 12/1991 | Brimm et al. |
| 5,077,666 A | 12/1991 | Brimm et al. |
| 5,086,391 A | 2/1992 | Chambers |
| 5,109,399 A | 4/1992 | Thompson |
| 5,122,959 A | 6/1992 | Nathanson et al. |

(Continued)

FOREIGN PATENT DOCUMENTS

JP  2003-109162  4/2003

(Continued)

OTHER PUBLICATIONS

Radosevich, Lynda, "Network holds sway on life, death," Computerworld, v27 n21, May 24, 1993, 2 pgs.

(Continued)

*Primary Examiner* — Gerald Gauthier
*Assistant Examiner* — Simon King
(74) *Attorney, Agent, or Firm* — John R. Thompson; Stoel Rives LLP

(57) ABSTRACT

A system and method to assist an emergency medical dispatcher in responding to emergency calls. A computer implemented emergency dispatch protocol includes interrogatories for a dispatcher to ask a caller to generate an appropriate response. A diagnostic tool is provided to diagnosis as to whether a patient has likely suffered a stroke. The diagnostic tool determines whether the patient has likely suffered a stroke based on caller-relayed information about the patient. The diagnostic tool can be launched automatically by the emergency dispatch protocol, or manually by a dispatcher. The diagnostic tool presents a user interface that provides, among other things, instructions, questions, and input fields.

29 Claims, 14 Drawing Sheets

U.S. PATENT DOCUMENTS

| | | | |
|---|---|---|---|
| 5,193,855 A | 3/1993 | Shamos | |
| 5,228,449 A | 7/1993 | Christ et al. | |
| 5,253,164 A | 10/1993 | Holloway et al. | |
| 5,255,187 A | 10/1993 | Sorensen | |
| 5,291,399 A | 3/1994 | Chaco | |
| 5,323,444 A | 6/1994 | Ertz et al. | |
| 5,339,351 A | 8/1994 | Hoskinson et al. | |
| 5,348,008 A | 9/1994 | Bornn et al. | |
| 5,379,337 A | 1/1995 | Castillo et al. | |
| 5,404,292 A | 4/1995 | Hendrickson | |
| 5,410,471 A | 4/1995 | Alyfuku et al. | |
| 5,423,061 A | 6/1995 | Fumarolo et al. | |
| 5,438,996 A | 8/1995 | Kemper et al. | |
| 5,441,047 A | 8/1995 | David et al. | |
| 5,462,051 A | 10/1995 | Oka et al. | |
| 5,471,382 A | 11/1995 | Tallman et al. | |
| 5,502,726 A | 3/1996 | Fischer | |
| 5,513,993 A | 5/1996 | Lindley et al. | |
| 5,516,702 A | 5/1996 | Senyei et al. | |
| 5,521,812 A | 5/1996 | Feder et al. | |
| 5,536,084 A | 7/1996 | Curtis et al. | |
| 5,544,649 A | 8/1996 | David et al. | |
| 5,554,031 A | 9/1996 | Moir et al. | |
| 5,590,269 A | 12/1996 | Kruse et al. | |
| 5,594,638 A | 1/1997 | Iliff | |
| 5,594,786 A | 1/1997 | Chaco et al. | |
| 5,596,994 A | 1/1997 | Bro | |
| 5,630,125 A | 5/1997 | Zellweger | |
| 5,636,873 A | 6/1997 | Sonsteby | |
| 5,650,995 A | 7/1997 | Kent | |
| 5,660,176 A | 8/1997 | Iliff | |
| 5,675,372 A | 10/1997 | Aguayo, Jr. et al. | |
| 5,682,419 A | 10/1997 | Grube et al. | |
| 5,684,860 A | 11/1997 | Milani et al. | |
| 5,689,229 A | 11/1997 | Chaco et al. | |
| 5,719,918 A | 2/1998 | Serbetciouglu et al. | |
| 5,722,418 A | 3/1998 | Bro | |
| 5,724,983 A | 3/1998 | Selker et al. | |
| 5,734,706 A | 3/1998 | Windsor et al. | |
| 5,745,532 A | 4/1998 | Campana, Jr. | |
| 5,748,907 A | 5/1998 | Crane | |
| 5,754,960 A | 5/1998 | Downs et al. | |
| 5,759,044 A | 6/1998 | Redmond | |
| 5,761,278 A | 6/1998 | Pickett et al. | |
| 5,761,493 A | 6/1998 | Blakeley et al. | |
| 5,787,429 A | 7/1998 | Nikolin, Jr. | |
| 5,805,670 A | 9/1998 | Pons et al. | |
| 5,809,493 A | 9/1998 | Ahamed et al. | |
| 5,822,544 A | 10/1998 | Chaco et al. | |
| 5,823,948 A | 10/1998 | Ross, Jr. et al. | |
| 5,826,077 A | 10/1998 | Blakeley et al. | |
| 5,832,187 A | 11/1998 | Pedersen et al. | |
| 5,842,173 A | 11/1998 | Strum et al. | |
| 5,844,817 A | 12/1998 | Lobley et al. | |
| 5,850,611 A | 12/1998 | Krebs | |
| 5,857,966 A * | 1/1999 | Clawson | 600/300 |
| 5,901,214 A | 5/1999 | Shaffer et al. | |
| 5,902,234 A | 5/1999 | Webb | |
| 5,910,987 A | 6/1999 | Ginter et al. | |
| 5,912,818 A | 6/1999 | McGrady et al. | |
| 5,915,019 A | 6/1999 | Ginter et al. | |
| 5,926,526 A | 7/1999 | Rapaport et al. | |
| 5,933,780 A | 8/1999 | Connor et al. | |
| 5,961,446 A | 10/1999 | Beller et al. | |
| 5,962,891 A | 10/1999 | Arai | |
| 5,964,700 A | 10/1999 | Tallman et al. | |
| 5,986,543 A | 11/1999 | Johnson | |
| 5,989,187 A | 11/1999 | Clawson | |
| 5,991,730 A | 11/1999 | Lubin et al. | |
| 5,991,751 A | 11/1999 | Rivette et al. | |
| 6,004,266 A | 12/1999 | Clawson | |
| 6,010,451 A | 1/2000 | Clawson | |
| 6,022,315 A | 2/2000 | Iliff | |
| 6,035,187 A | 3/2000 | Franza | |
| 6,040,770 A | 3/2000 | Britton | |
| 6,052,574 A | 4/2000 | Smith, Jr. | |
| 6,053,864 A | 4/2000 | Clawson | |
| 6,058,179 A | 5/2000 | Shaffer et al. | |
| 6,074,345 A | 6/2000 | van Oostrom et al. | |
| 6,076,065 A | 6/2000 | Clawson | |
| 6,078,894 A | 6/2000 | Clawson et al. | |
| 6,106,459 A | 8/2000 | Clawson | |
| 6,112,083 A | 8/2000 | Sweet et al. | |
| 6,115,646 A | 9/2000 | Fiszman et al. | |
| 6,117,073 A | 9/2000 | Jones et al. | |
| 6,118,866 A | 9/2000 | Shtivelman | |
| 6,127,975 A | 10/2000 | Maloney | |
| 6,134,105 A | 10/2000 | Lueker | |
| 6,292,542 B1 | 9/2001 | Bilder | |
| 6,370,234 B1 | 4/2002 | Kroll | |
| 6,535,121 B2 | 3/2003 | Matheny | |
| 6,594,634 B1 | 7/2003 | Hampton et al. | |
| 6,607,481 B1 | 8/2003 | Clawson | |
| 6,610,012 B2 | 8/2003 | Mault | |
| 6,696,956 B1 | 2/2004 | Uchida et al. | |
| 6,879,819 B2 | 4/2005 | Brooks | |
| 6,901,397 B1 | 5/2005 | Moldenhauer et al. | |
| 6,931,112 B1 | 8/2005 | McFarland et al. | |
| 6,968,375 B1 | 11/2005 | Brown | |
| 7,106,835 B2 | 9/2006 | Saalsaa | |
| 7,194,395 B2 | 3/2007 | Genovese | |
| 7,289,944 B1 | 10/2007 | Genovese | |
| 7,428,301 B1 | 9/2008 | Clawson | |
| 7,436,937 B2 | 10/2008 | Clawson | |
| 7,645,234 B2 | 1/2010 | Clawson | |
| 7,703,020 B2 | 4/2010 | Bhattaru | |
| 7,783,586 B2 | 8/2010 | Friedlander et al. | |
| 2002/0004729 A1 | 1/2002 | Zak et al. | |
| 2002/0106059 A1 | 8/2002 | Kroll et al. | |
| 2003/0028536 A1 | 2/2003 | Singh et al. | |
| 2003/0050538 A1 | 3/2003 | Naghavi et al. | |
| 2003/0187615 A1 | 10/2003 | Epler et al. | |
| 2003/0195394 A1 | 10/2003 | Saalsaa | |
| 2003/0212575 A1 | 11/2003 | Saalsaa et al. | |
| 2006/0059423 A1 | 3/2006 | Lehmann et al. | |
| 2006/0122520 A1 | 6/2006 | Banet et al. | |
| 2006/0167346 A1 | 7/2006 | Sarel | |
| 2006/0173500 A1 | 8/2006 | Walker et al. | |
| 2006/0178908 A1 | 8/2006 | Rappaport | |
| 2006/0212315 A1 | 9/2006 | Wiggins | |
| 2007/0055559 A1 | 3/2007 | Clawson | |
| 2007/0112275 A1 | 5/2007 | Cooke et al. | |
| 2007/0116189 A1 | 5/2007 | Clawson | |
| 2007/0201664 A1 | 8/2007 | Salafia et al. | |
| 2009/0168975 A1 | 7/2009 | Clawson | |
| 2009/0191529 A1 | 7/2009 | Mozingo et al. | |
| 2010/0004710 A1 | 1/2010 | Kellum | |
| 2010/0121156 A1 | 5/2010 | Yoo | |
| 2010/0152800 A1 | 6/2010 | Walker et al. | |
| 2010/0198755 A1 | 8/2010 | Soll et al. | |
| 2010/0257250 A1 | 10/2010 | Salafia et al. | |

FOREIGN PATENT DOCUMENTS

| | | |
|---|---|---|
| JP | 2003-187003 A | 7/2003 |
| JP | 2003-256963 | 12/2003 |
| JP | 2010-033201 | 12/2010 |
| KR | 10-2005-0085778 A | 8/2005 |
| KR | 10-2006-0084866 A | 7/2006 |
| KR | 2007-0043337 | 4/2007 |
| KR | 10-2008-0004125 A | 1/2008 |
| WO | WO2006/015229 A2 | 2/2006 |
| WO | WO2008/156876 A1 | 12/2008 |

OTHER PUBLICATIONS

Harris, Roger, "Updated 911 Phone System Top Concern of Residents," Business First-Louisville, v9 n19 s1, Dec. 1992, 3 pgs.

"Geac Completes Software Install," Wireless Week, Nov. 18, 1996, 3 pgs.

"Dictaphone introduces Windows-based Computer-Aided Dispatch (CAD) system," Business Wire, Apr. 23, 1996, 2 pgs. (in commercial use in 1995).

Holroyd, Brian, et al., "Medical Control; Quality Assurance in Prehospital Care," JAMA, the Journal of American Medical Association, v256, n8, Aug. 1986, p. 1027-1031.

CBS web page News Story entitled "911 Operator: 'It's got to be Hell'", Mar. 31, 2006 (excerpts from 911 operators' actions during the attacks on Sep. 11, 2001), 3 pgs.
Best, Wendy, "999 United Emergency services share life-saving Role to boost response," Western Daily Press, WDP Severnside ed., May 27, 1999, 2 pgs.
Poellmitz, William C., "Wireless technology keeps public safety a step ahead," Nation's Cities Weekly, v21 n17, Apr. 27, 1998, 3 pgs.
Crowley, Mark, "Learning from CAD System Implementation," Communications, v29 n8, Aug. 1992, 5 pgs.
Anonymous, "Suburban Chicago towns centralize 911 services," Communications News, v31 n10, Oct. 1994, 2 pgs.
Office Action Summary from USPTO for U.S. Appl. No. 10/255,901 mailed Dec. 31, 2003, 8 pgs.
Office Action Summary from USPTO for U.S. Appl. No. 10/255,901 mailed Oct. 13, 2004, 8 pgs.
Office Action Summary from USPTO for U.S. Appl. No. 10/255,901 mailed Jun. 29, 2005, 7 pgs.
Advisory Action Before the Filing of an Appeal Brief from USPTO for U.S. Appl. No. 10/255,901 mailed Feb. 14, 2006, 3 pgs.
Office Action Summary from USPTO for U.S. Appl. No. 10/255,901 mailed Jun. 7, 2006, 8 pgs.
Office Action Summary from USPTO for U.S. Appl. No. 10/255,901 mailed Feb. 27, 2007, 8 pgs.
Office Action Summary from USPTO for U.S. Appl. No. 10/255,901 mailed Sep. 6, 2007, 9 pgs.
Office Action Summary from USPTO for U.S. Appl. No. 10/255,905 mailed May 19, 2004, 7 pgs.
Office Action Summary from USPTO for U.S. Appl. No. 10/255,905 mailed May 26, 2005, 5 pgs.
Office Action Summary from USPTO for U.S. Appl. No. 10/255,905 mailed Feb. 9, 2006, 8 pgs.
Advisory Action Before the Filing of an Appeal Brief from USPTO for U.S. Appl. No. 10/255,905 mailed Aug. 11, 2006, 3 pgs.
Office Action Summary from USPTO for U.S. Appl. No. 10/255,905 mailed Jan. 30, 2007, 7 pgs.
Notice of Non-Compliant Amendment (37 CFR 1.121) from USPTO for U.S. Appl. No. 10/255,905 mailed Jul. 9, 2007, 4 pgs.
Office Action Summary from USPTO for U.S. Appl. No. 10/255,905 mailed Oct. 5, 2007, 7 pgs.
Office Action Summary from USPTO for U.S. Appl. No. 09/685,697 mailed Jul. 18, 2003, 8 pgs.
Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.
Office Action Summary from USPTO for U.S. Appl. No. 10/140,635 mailed Oct. 3, 2003, 9 pgs.
Office Action Summary from USPTO for U.S. Appl. No. 10/140,635 mailed Jul. 16, 2004, 11 pgs.
Office Action Summary from USPTO for U.S. Appl. No. 10/140,635 mailed Apr. 19, 2005, 11 pgs.
Office Action Summary from USPTO for U.S. Appl. No. 10/140,635 mailed Jan. 17, 2006, 13 pgs.
Office Action Summary from USPTO for U.S. Appl. No. 10/140,635 mailed Sep. 20, 2006, 15 pgs.
Office Action Summary from USPTO for U.S. Appl. No. 10/140,635 mailed Jun. 21, 2007, 15 pgs.
International Search Report for PCT/US2008/054987 filed on Feb. 26, 2008, and mailed on Oct. 8, 2008, 2 pgs.
Written Opinion of the International Searching Authority for PCT/US2008/054987 filed on Feb. 26, 2008, and mailed on Oct. 8, 2008, 9 pgs.
Notification of Transmittal of the International Search Report (2 pgs.), International Search Report, (2 pgs.), and Written Opinion (8 pgs.) mailed from International Searching Authority on Jun. 10, 2009.
International Search Report and Written Opinion for PCT/US09/48577, International filed Jun. 25, 2009, mailed from ISA Aug. 7, 2009, 9 pgs.
Office Action for U.S. Appl. No. 12/268,963, filed Nov. 11, 2008, mailed from USPTO on Jul. 29, 2011, 18 pgs.
Office Action for U.S. Appl. No. 12/396,201, filed Mar. 2, 2009 and mailed from USPTO on Mar. 8, 2011, 23 pgs.
International Search Report and Written Opinion mailed Jan. 19, 2011 in PCT Application No. PCT/US2010/043308, filed Jul. 27, 2010.
International Search Report and Written Opinion mailed Jan. 19, 2011 in PCT Application No. PCT/US2010/043311, filed Jul. 27, 2010.
International Search Report and Written Opinion for PCT/US2012/021867 filed Jan. 19, 2012, and mailed Aug. 30, 2012, 9 pgs.
United States Patent Office, Office Action for U.S. Appl. No. 12/558,808, mailed Apr. 23, 2011.
International Search Report and Written Opinion PCT/US2010/050402, filed on Sep. 27, 2010, and mailed from ISA on Apr. 27, 2011, 9 pgs.
International Preliminary Report of Patentability for PCT/US2009/048577 filed on Jun. 25, 2009 mailed Oct. 27, 2011, 7 pgs.
International Search Report and Written Opinion for PCT/US2011/042543 filed on Jun. 30, 2011, and mailed from ISA on Feb. 9, 2012, 11 pgs.
International Search Report and Written Opinion for PCT/US2011/042582 filed on Jun. 30, 2011, and mailed from ISA on Feb. 9, 2012, 8 pgs.
International Preliminary Report of Patentability for PCT/US2010/043308 filed on Jul. 27, 2010 mailed Mar. 22, 2012, 6 pgs.
International Preliminary Report of Patentability for PCT/US2010/043311 filed on Jul. 27, 2010 mailed Mar. 29, 2012, 6 pgs.
Office Action Summary from USPTO for U.S. Appl. No. 12/422,561 mailed Jul. 3, 2012, 23 pgs.

* cited by examiner

STROKE DIAGNOSTIC AND INTERVENTION TOOL FOR EMERGENCY DISPATCH

COPYRIGHT NOTICE

©2009 Priority Dispatch Corp. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71 (d).

TECHNICAL FIELD

This invention relates to computer systems and methods for providing medical protocol interrogation, instruction, and emergency dispatch. More specifically, the invention is directed to computer-implemented tools to assist a dispatcher during an interrogation and instruction of an emergency caller.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Figure 1:
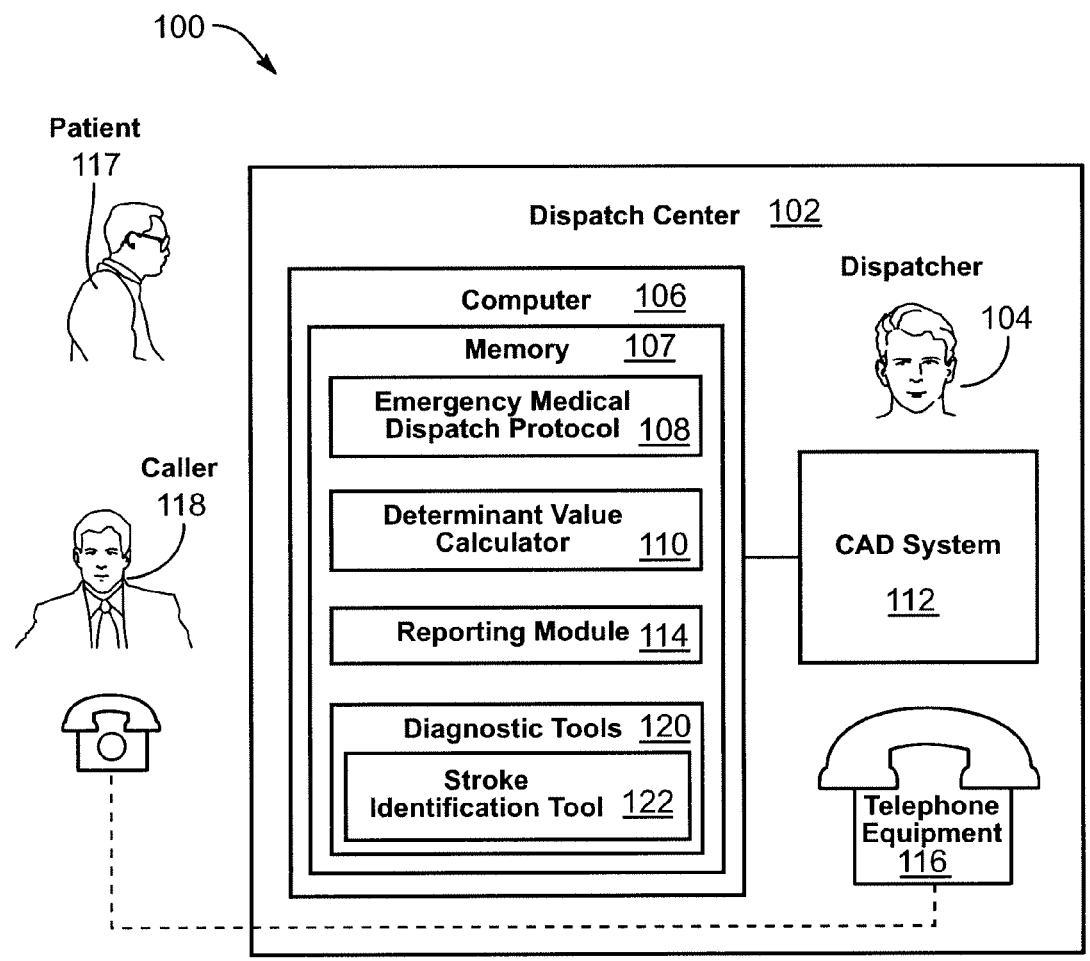
FIG. 1 is a block diagram of an emergency dispatch system, according to one embodiment.

Emergency dispatchers handle emergency calls reporting a wide variety of emergency situations. An automated emergency dispatch system, potentially implemented on a computer, can aid a dispatcher in prioritizing the calls and processing the calls to generate an appropriate emergency dispatch response. Regardless of the experience or skill level of the dispatcher, the automated emergency dispatch systems can enable a consistent and predictable emergency dispatch response, despite the diverse aspects of emergency situations, including inter alia signs, symptoms, conditions, and circumstances, that may be reported from one call to the next.

Although an automated emergency dispatch system can enable collection and processing of widely divergent aspects of emergency situations, some of the emergency situations and/or aspects reported should be explored in greater depth as they are reported. This further exploration may require the dispatcher to probe more deeply to gather more descriptive details. Moreover, some emergency situations may be improved by more detailed instructions. Still other emergency situations may involve a clinical presentation of a condition that is not easily diagnosed, but which could alter the appropriate dispatch response if properly diagnosed.

A dispatcher with little or no medical training or experience likely cannot properly explore situations and/or aspects or diagnose medical conditions, let alone instruct a caller to do so. Furthermore, the automated emergency dispatch systems are not equipped to assist or enable a dispatcher to explore situations in greater depth, to provide further instruction, nor to diagnose conditions. Accordingly, the present disclosure is directed to diagnostic tools that supplement an automated emergency dispatch system to attempt to address these and other shortcomings of automated emergency dispatch systems.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer executable code located within a memory device and/or computer-readable storage medium. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

An emergency dispatch system as disclosed herein may be computer-implemented in whole or in part on a digital computer. The digital computer includes a processor performing the required computations. The computer further includes a memory in electronic communication with the processor for storing a computer operating system. The computer operating systems may include MS-DOS, Windows, Unix, AIX, CLIX, QNX, OS/2, and Apple. Alternatively, it is expected that future embodiments will be adapted to execute on other future operating systems. The memory also stores application programs including a Computer Aided Dispatch (CAD) program, an automated emergency dispatch protocol, a user interface program, and data storage. The computer may further include an output device, such as a display unit, for viewing the displayed instructions and inquiries and a user input device for inputting response data.

FIG. 1 is an emergency dispatch system 100, according to one embodiment. At a dispatch center 102, a dispatcher 104 operates a computer 106. The computer may include a memory 107 to store protocols, modules, tools, data, etc. The computer may be configured to execute an emergency medical dispatch protocol 108 to enable the dispatcher to rapidly and consistently address a medical emergency of a patient 117 as reported by a caller 118. The emergency medical dispatch protocol 108 provides a logic tree with questions, possible responses from a caller 118, and instructions to the caller 118. The responses may route to subsequent questions and/or instructions to the caller. The responses are processed according to predetermined logic to both provide to the dispatcher 104 the correct emergency medical dispatch response (e.g., by trained emergency responders) and the appropriate doctor-approved post-dispatch instructions for relay to the caller 118 before professional help arrives at the scene. The emergency medical dispatch system 100 may also aid the dispatcher in determining an appropriate priority of the emergency call, including but not limited to a priority of the emergency call relative to other emergency calls.

Although an emergency medical dispatch system 100 and emergency medical dispatch protocol 108 are disclosed and described herein, a person of ordinary skill can appreciate that other emergency dispatch systems and emergency dispatch protocols are contemplated, including but not limited to emergency fire dispatch systems and protocols and emergency police dispatch systems and protocols. Exemplary embodiments of such emergency dispatch systems and protocols are disclosed in U.S. Pat. Nos. 5,857,966, 5,989,187, 6,004,266, 6,010,451, 6,053,864, 6,076,065, 6,078,894, 6,106,459, 6,607,481, 7,106,835, and 7,428,301, which are incorporated herein by reference.

The computer 106 may also operate a determinant value calculator 110 to calculate a determinant value from the responses of the caller 118 to protocol questions. The computer 106 presents the determinant value to generate an appropriate emergency dispatch response and/or establish the priority of the emergency call. The response may include dispatching professional emergency responders to the scene of the emergency. Because the questions asked and the recommendations that are made deal directly with life and death decisions, the protocols used shall have passed through a rigorous medical review by a panel of doctors and EMS public safety experts who specialize in emergency medicine. The determinant value calculator 110 may be stored on the memory 107 of the computer.

Many calls for medical services are not true medical emergencies, so it is important to prioritize the calls in several ways. First, calls that are true emergencies should be dispatched first. Second, if an agency has units with different capabilities, the more advanced units should be sent to more severe medical problems. And finally, if lights-and-siren are not needed from a medical standpoint, they should not be used, thereby increasing the safety of all those on the road and in the emergency vehicles. While many medical calls are not true emergencies, all situations can benefit from medical evaluation and instruction. Prior to the arrival of professional help on-scene, the emergency medical dispatch protocol 108 provides the dispatcher 104 with instructions for the caller 118 that are appropriate to the type of call, from a patient 117 with minor lacerations to a patient 117 who is not breathing.

The determinant value provides a categorization code of the type and level of the incident. The code may be provided to a Computer Aided Dispatch (CAD) system 112, which is a tool used by a dispatcher 104 to track and allocate emergency response resources, for processing. The CAD system 112 may operate in whole or in part on a separate computer in communication with computer 106. In another embodiment, the CAD system 112 operates on computer 106. The primary information used by the CAD system 112 is location information of both the incident and units, unit availability and the type of incident. The CAD system 112 may use third party solutions, such as E-911, vehicle location transponders and MDT's for automating the location and availability tasks.

The computer 106 may also include a reporting module 114 to statistically measure the performance of individual staff and overall performance of the dispatch center 102. These statistics include compliance rates, call processing statistics, and peer measurements. The reporting module 114 may be stored on the memory 107 of the computer 106.

The computer 106 may further comprise an input device such as a keyboard, mouse, or other input device and also an output device such as a display monitor. The input device receives input from a user (generally a dispatcher) and provides it to the emergency medical dispatch system 100. The input may be provided to the computer 106, the emergency protocol 108, the diagnostic tools 120, and/or the CAD system 112. The output device receives output from the emergency medical dispatch system 100 and displays or otherwise presents the output to the user. In another embodiment, the input device and output device are provided by the CAD system 112. In still another embodiment, the CAD system 112 runs on computer 106.

The dispatch center 102 includes telephony equipment 116 to answer emergency calls. A call into the dispatch center 102 from a caller 118 initiates creation of a medical call incident. The dispatcher 104 identifies the call as requiring an emergency medical dispatch, and the emergency medical dispatch protocol 108 is accessed. The protocol 108 may provide instructions that are expertly drafted to assist a novice caller 118 in diagnosing a condition of a patient 117. The protocol 108 may also provide expertly drafted first aid instructions to assist a patient 117 prior to the arrival of trained emergency responders. The instructions may be vocally relayed by the dispatcher 104 to the caller 118 over the telephony equipment 116.

Some protocol questions may be readily answerable by the caller 118, whereas others are more difficult to answer. Certain diagnostic inquiries may be difficult for the untrained caller to determine or may be difficult to answer under the stress of an emergency situation. Accordingly, in addition to instructions, the emergency medical dispatch system 100 may provide one or more computer-implemented diagnostic tools 120. The diagnostic tools 120 may greatly improve information collection and intervention for emergency medical response situations and aid in saving lives.

A diagnostic tool 120 may aid the dispatcher and/or the caller (via instructions from the dispatcher) in diagnosing a condition of a patient 104. A diagnostic tool 120 may also be an interventional tool, providing instructions that direct a caller to intervene, or take action, to treat a patient 104, or otherwise change the circumstances or conditions of an emergency situation. For sake of clarity, diagnostic tools and interventional tools are both referred to herein generally as diagnostic tools. Accordingly, a diagnostic tool 120, as referred to herein, may provide diagnostic instructions, interventional instructions, or both diagnostic and interventional instructions. Whether a diagnostic tool 120 provides merely diagnostic instructions, merely interventional instructions, or both diagnostic and interventional instructions, the diagnostic tool can provide consistent and reliable instruction, information gathering, and/or timing for a particular emergency situation.

The diagnostic tools 120 are computer implemented software modules that enable a dispatcher 104 to provide consistent, expert advice to assist a caller with regards to a particular aspect of an emergency situation, such as determining a vital sign. One benefit of the diagnostic tools 120 is the computer aided timing of techniques to determine the vital signs. In highly stressful conditions, the diagnostic tools 120 provide a necessary resource to reading critical signs. The diagnostic tools 120 may be stored in the memory 107 of the computer 106 and initiated and executed as required. The diagnostic tools 120 may be embodied as computer executable software applications and associated data.

The emergency medical dispatch protocol 108 may call on a diagnostic tool 120, for example to assist with an interrogatory, and may route to the appropriate diagnostic tool 120 when needed. When directed according to the protocol 108, the emergency medical dispatch system 100 may automatically, i.e., without dispatcher intervention, initiate the appropriate diagnostic tool 120 on the dispatch center computer 106. This may occur when the emergency medical dispatch protocol 108 arrives at a diagnosis step in the protocol and initiates a corresponding diagnostic tool 120. The emergency dispatch system 100 may also allow the dispatcher 104 the option to manually call upon a diagnostic tool 120 as desired. Icons and/or buttons may be displayed in a tool bar, or other convenient location on a user interface to allow the dispatcher 104 to initiate a corresponding diagnostic tool 120. In another embodiment, the emergency medical dispatch protocol 108 may simply prompt the dispatcher to launch the stroke identification tool 122 when needed.

The diagnostic tool 120 discussed herein comprises a stroke identification tool 122. The stroke identification tool 122 is configured to assist the dispatcher 104 in guiding the caller 118 to diagnose whether the patient 117 may have suffered a stroke. The emergency medical dispatch protocol 108 may automatically route directly to the stroke identification tool 122 upon receipt of information indicating the patient may have suffered a stroke. The emergency medical dispatch protocol 108 may also enable a dispatcher to manually launch the stroke identification tool. The stroke identification tool 122 is discussed in reference to figures of graphical user interfaces that exemplify certain embodiments. One of skill in the art will appreciate that such interfaces may be implemented and designed in various ways and still be within the scope of the invention.

Figure 2:
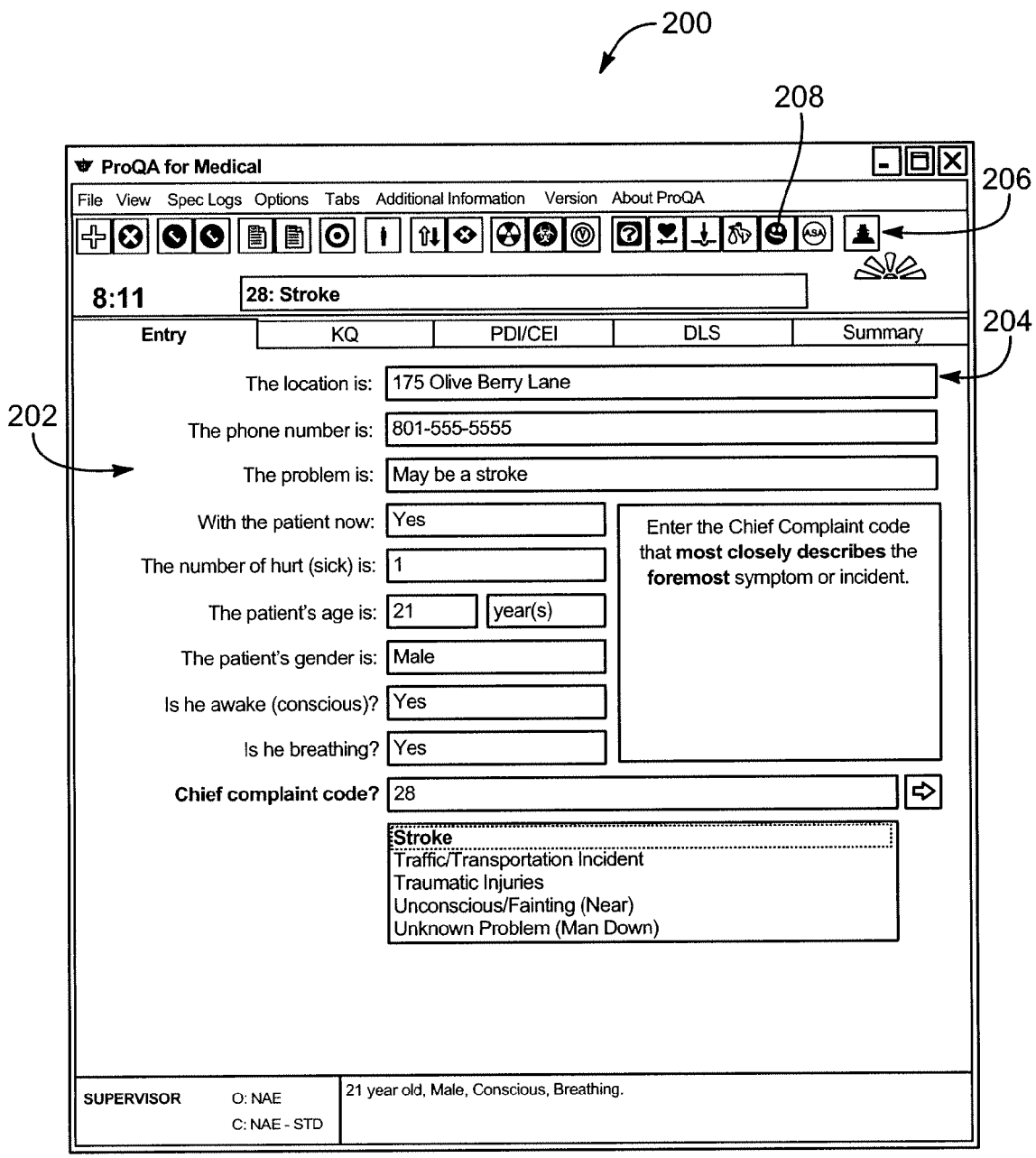
FIG. 2 illustrates a user interface of an emergency medical dispatch protocol, according to one embodiment.

FIG. 2 illustrates a user interface 200 of an emergency medical dispatch protocol, according to one embodiment. The emergency medical dispatch protocol user interface 200 allows a dispatcher to interface with the emergency medical dispatch protocol. The emergency medical dispatch protocol may present interrogatories 202 via the emergency medical dispatch protocol user interface 200. The interrogatories 202 are provided for the dispatcher to direct to the caller to gather information regarding the medical emergency of the patient. The dispatcher and/or the emergency medical dispatch system may gather the information in the form of caller responses to the interrogatories 202. The dispatcher may input the responses of the caller to the interrogatories into response fields 204 provided by the user interface 200. The response fields 204 may include, for example, familiar user interface components, including but not limited to text fields, text boxes, menus, drop-down menus, drop-down selection boxes, lists, buttons, check boxes, and radio buttons. The response fields 204 may correspond to information indicative of one or more responses of the caller to the interrogatories 202.

The caller responses, and information therein, relayed from the caller to the dispatcher, and input into the system, may be used by the emergency medical protocol to determine subsequent interrogatories 202 and instructions to present to the dispatcher. The caller responses, and information therein, may indicate the caller's observations of signs and symptoms of the patient's medical condition. The information gathered from the caller responses may be used by the emergency medical dispatch system to generate an emergency medical dispatch response by trained emergency responders. The information gathered from the caller responses may be used by the determinant value calculator to calculate a determinant value that can be communicated to the emergency responders. Further details of emergency medical dispatch protocols and user interfaces to interact with the same can be found in the earlier referenced U.S. patents.

The emergency medical dispatch protocol user interface 200 may also provide one or more diagnostic tool launch inputs 206. As illustrated, one or more buttons may be provided on the user interface as diagnostic tool launch inputs 206. The diagnostic tool launch inputs 206 enable the dispatcher to launch a particular diagnostic tool. Although the emergency medical dispatch protocol may automatically initiate a diagnostic tool based on dispatcher-entered input indicative of one or more responses of the caller, the diagnostic tool launch inputs 206 provide a way for the dispatcher to manually (i.e. any time, at the dispatcher's discretion) initiate a diagnostic tool. In FIG. 2, a stroke identification tool launch input 208 is provided. The stroke identification tool launch input 208 may comprise a button on the emergency medical dispatch protocol user interface 200 with an icon of a face with mouth sagging on one side. The icon may indicate that the button launches the stroke identification tool. As will be appreciated by a person of ordinary skill, the diagnostic tool launch inputs 206 may comprise a component other than a button, including familiar user interface components, such as a drop down menu, a drop down selection box, a list, a check box, a text field, and a radio button.

FIGS. 3A-3F illustrate an embodiment of a user interface 300 of a stroke identification tool, according to one embodiment. The user interface 300 of the illustrated embodiment provides instructions 302, 304, 306, 308, a start input 310, questions 312, 314, 316, 318, input fields 320, 322, 324, a finished input 326, a recommendation field 328, and a close input 330. The user interface 300 aids a dispatcher in guiding a caller in obtaining information that can be used by the stroke identification tool to diagnose whether a patient has suffered a stroke. The instructions 304, 306, 308, the questions 312, 314, 316, and the input fields 320, 322, 324 may be grouped into one or more scripted interactions (e.g., at least one instruction, at least one question, and at least one input field).

A scripted interaction guides the dispatcher in guiding the caller to identify signs and symptoms that a patient may have suffered a stroke. The user interface 300 may further provide answer fields 334, 336, 338 to display an answer number that corresponds to a patient response that may be selected in each input field 320, 322, 324 (i.e. the input provided to the user interface by the dispatcher that corresponds to the caller's answers to the questions 312, 314, 316 and also the patient's responses to the instructions 302, 304, 306, 308). The user interface 300 may also provide one or more confirming instructions 332 to confirm the status of the caller and one or more interaction instructions 340, 342, 344, 346 intended solely for the dispatcher as guidance in interacting with the caller.

The instructions 302, 304, 306, 308 may direct the dispatcher in guiding the caller. An initial instruction 302 may direct the dispatcher to prepare the caller for subsequent diagnostic instructions 304, 306, 308 and/or questions 312, 314, 316, 318. For example, the initial instruction 302 may provide, "I want you to get close enough to ask her/him three questions." The initial instruction 302 may also prepare the caller to facilitate diagnosing whether the patient may have suffered a stroke. A confirming instruction 332 may be provided, such as "Tell me when you are ready," to enable the dispatcher to know when the caller is prepared for the additional diagnostic instructions 304, 306, 308.

Figure 3A:
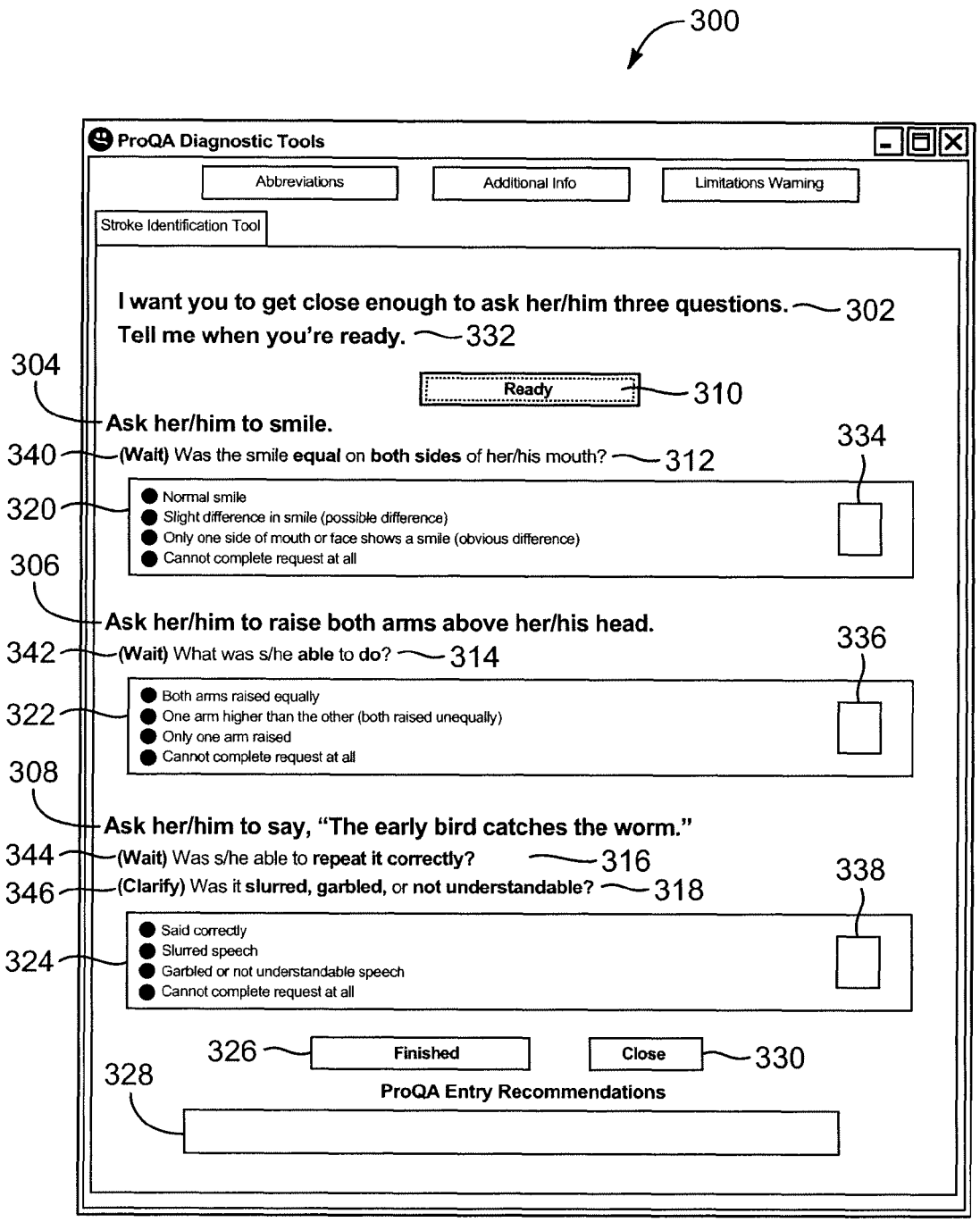
FIGS. 3A-3F illustrates a user interface of a stroke identification tool.

The start input 310 may be provided to activate the diagnostic function of the stroke identification tool. FIG. 3A illustrates the user interface 300 prior to a start input 310 activating diagnostic function of the stroke identification tool. In the embodiment of FIG. 3A, the start input 310 is a button. The start input 310 is labeled with the term "Ready," indicating to the dispatcher in an intuitive manner that the dispatcher should click the button when the caller responds to the confirming instruction 332 that the caller is ready. Prior to the start input 310 being clicked, the components of the user interface 300 may be inactive. For example, in the depicted embodiment the input fields 320, 322, 324 are darkened and/or grayed out (i.e., displayed with a lighter shade of gray instead of black or colors, to indicate that it cannot currently be operated by the user) because they are inactive. The answer fields 334, 336, 338 are also blank, indicating they are inactive. A person of ordinary skill will appreciate that, prior to the start input 310 being clicked, other components such as the diagnostic instructions 304, 306, 308, the finished input 326, the recommendation field 328, and the close input 330 may also be inactive and/or grayed out. After the start input 310 is clicked, these components may be activated. In another embodiment, these components may be activated at various stages of progression within the protocol of the diagnostic tool.

The input fields 320, 322, 324 of the illustrated embodiment are provided as groups of radio buttons. As can be appreciated, the input fields 320, 322, 324 may be provided as any of a variety of user interface components, including but not limited to text fields, text boxes, menus, drop-down menus, drop-down selection boxes, lists, buttons, and check boxes, or combinations thereof. The input fields are discussed in greater detail below with reference to FIGS. 3C-3E.

Figure 3B:
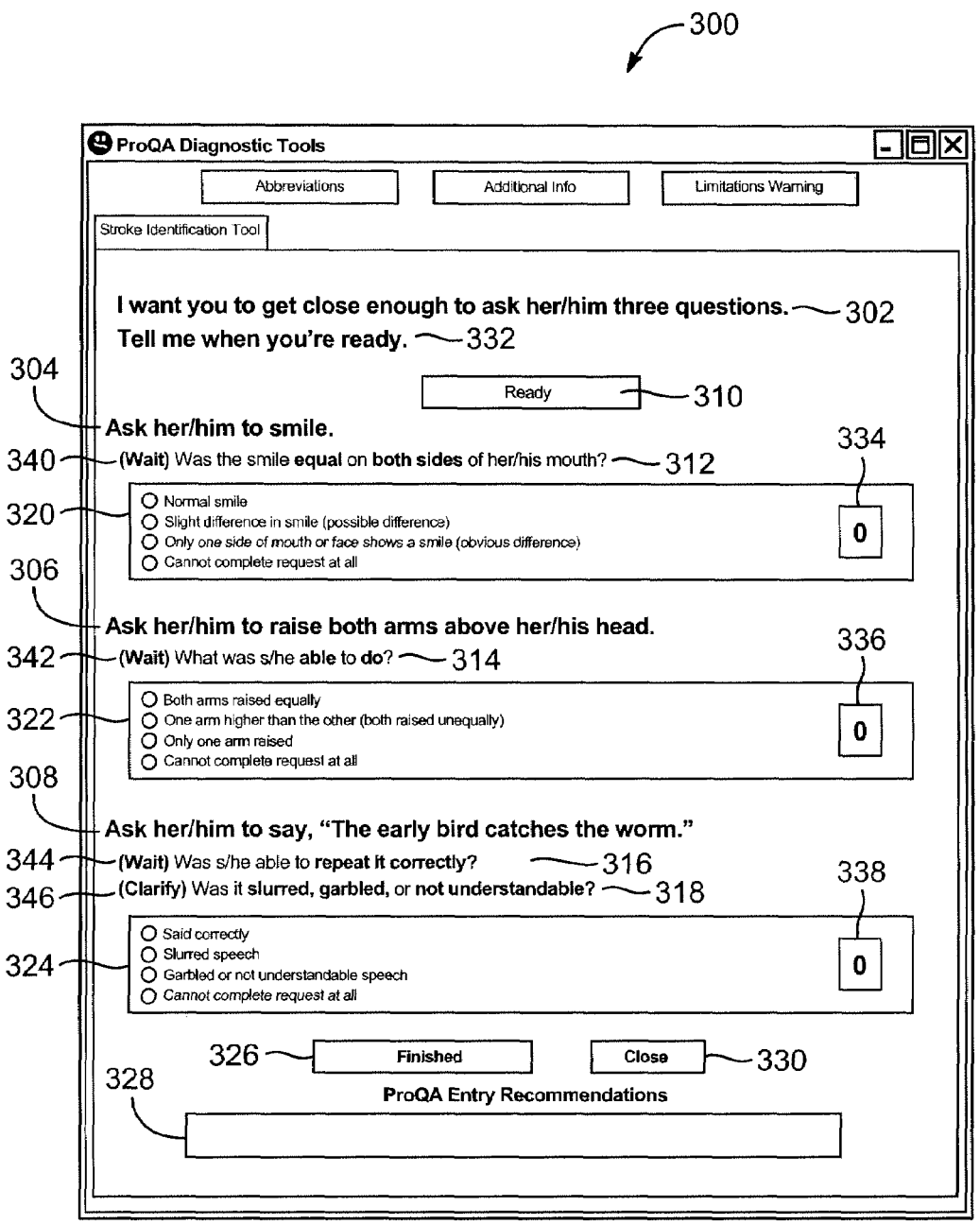

FIG. 3B illustrates the user interface 300 after the start input 310 has been clicked to activate diagnostic function of the stroke identification tool. After the start input 310 is clicked, the input fields 320, 322, 324 are no longer darkened, indicating they are activated. The answer fields 334, 336, 338 are also now active and show an answer number of "0" to indicate that no input has been provided. Other components, such as the finished input 326 and close input 330, that were previously in an inactive state may also be activated once the start input 310 has been clicked. In this manner, the progression of the protocol of the stroke identification tool can be controlled in an intuitive manner. The dispatcher is guided to wait until the caller is prepared for the diagnostic instructions 304, 306, 308. Moreover, by providing the input fields 320, 322, 324, the finished input 326, and the close input 330 in an inactive state prior to receiving the start input 310, the user interface 300 guards against the dispatcher inadvertently entering an input that is not indicative of the caller's observations of the patient.

Providing intuitive control of the progression of the protocol of the diagnostic tool can facilitate consistent and predictable processing of emergency calls. The intuitive progression generates predictable actions by the dispatcher despite the potential stress that may be involved with processing emergency calls and despite the skill level and/or experience of the dispatcher. The diagnostic tool enables a dispatcher with little or no experience and/or medical training to successfully determine, to a reasonable probability, whether a patient may have suffered a stroke.

Preventing inadvertent entering of an input that is not indicative of a caller observation can also be important in emergency dispatch scenarios. For example, a dispatcher may receive, and thereby be forced to process, multiple calls substantially at one time. The dispatcher may have provided a first caller multiple instructions, and progressed substantially along the protocol of the diagnostic tool, only to be disconnected due to the call being dropped. The situation associated with the dropped call may be ongoing, and the emergency medical dispatch system may allow the dispatcher to put the case on hold to await a call back from the first caller. The dispatcher may then answer a call expecting it to be the first caller, and instead discover a second caller is reporting an emergency. Accordingly, the dispatcher may initiate a new case (i.e., session or instance of the emergency medical dispatch protocol) and begin processing the second call. A short time later, the first caller may call back, and rather than starting over, the dispatcher will want to pick up processing of the emergency call substantially at the point in the stroke identification tool where the protocol was prior to the call being dropped.

Without guidance from the user interface 300 to indicate the point in the progression of the protocol, the stress and/or intensity of processing emergency calls may cause the dispatcher to forget where in the protocol the call was dropped. Moreover, as the dispatcher switches between the user interface associated with the first call and the user interface associated with the second call, there may be substantial risk that the dispatcher could click an area of the user interface and inadvertently select a response that does not indicate an observation of the particular caller associated with that user interface. The dispatcher may fail to recognize the inadvertent input or fail to realize that the inadvertent input is not indicative of an observation of the caller. Providing certain portions and components of the user interface 300 as initially inactive can help provide intuitive understanding of the point of progression in the protocol of the stroke identification tool and can guard against the dispatcher inadvertently providing inaccurate input.

After clicking the start input 310, the user interface 300 provides the dispatcher a diagnostic instruction 304 that the dispatcher can relay to the caller. The diagnostic instruction may be directed to guiding the caller in a manner that facilitates identifying a sign or symptom that the patient has suffered a stroke. For example, stroke victims commonly can suffer from numbness or weakness on one side of the body.

The numbness or weakness can cause a stroke victim to have a smile that sags or droops on one side. In the depicted embodiment, the diagnostic instruction 304 may direct the caller to, for example, "Ask her/him to smile," as a potential way for the caller to identify whether the patient may be experiencing any numbness or weakness. When the dispatcher relays this diagnostic instruction 304 to the caller, the caller is guided to ask the patient to smile.

An interaction instruction 340, such as "Wait," may be provided to guide the dispatcher in interacting with the caller. The interaction instruction 342 "Wait" instructs the dispatcher to allow the caller time to perform the diagnostic 304 instruction and observe the patient's response. The interaction instruction 340 may enhance consistent processing of emergency calls by prompting the dispatcher to be calm and patient despite the potential stress of processing the emergency call. The interaction instruction 340 may be provided in parentheses to indicate that it is intended solely for the dispatcher and is not to be relayed to the caller.

The user interface 300 may further provide a question 312 for the dispatcher to ask the caller to aid the caller in assessing the patient's response to the diagnostic instruction 304. The question 312 may also aid the dispatcher in gathering information about the caller's observations of the patient's response to the diagnostic instruction 304. The information gathered may be information concerning a potential sign or symptom of a stroke. For example, the question 312 provided by the user interface 300 may be, "Was the smile equal on both sides of his/her mouth?" to gather information about whether the patient may be experiencing any numbness or weakness. If the patient is unable to smile, or unable to smile equally on both sides of her/his mouth, the patient may be suffering from numbness or weakness that commonly results from a stroke. The caller vocally responds to the question over the telephone.

An input field 320 provided by the user interface allows the dispatcher to enter input that is indicative of the caller-relayed information conveyed in the caller's response to the question 312. Stated differently, the input field 320 may provide a way for the dispatcher to provide to the stroke identification tool information from the caller's response to the question 312. The caller-relayed information can indicate the caller's observations of the patient's response to the diagnostic instruction 304. In the depicted embodiment, user interface 300 provides the input field 320 as a group of radio buttons. Four radio buttons are provided, each button having an associated label providing a potential response of the caller, such as "Normal smile," "Slight difference in smile (possible difference)," "Only one side of mouth or face shows a smile (obvious difference)," and "Cannot complete request at all." The potential responses of the patient may correlate with a potential sign or symptom that the patient may have suffered a stroke. For example, the patient's inability to fully smile can indicate that the patient may be experiencing numbness or weakness, which often accompanies a stroke.

Figure 3C:
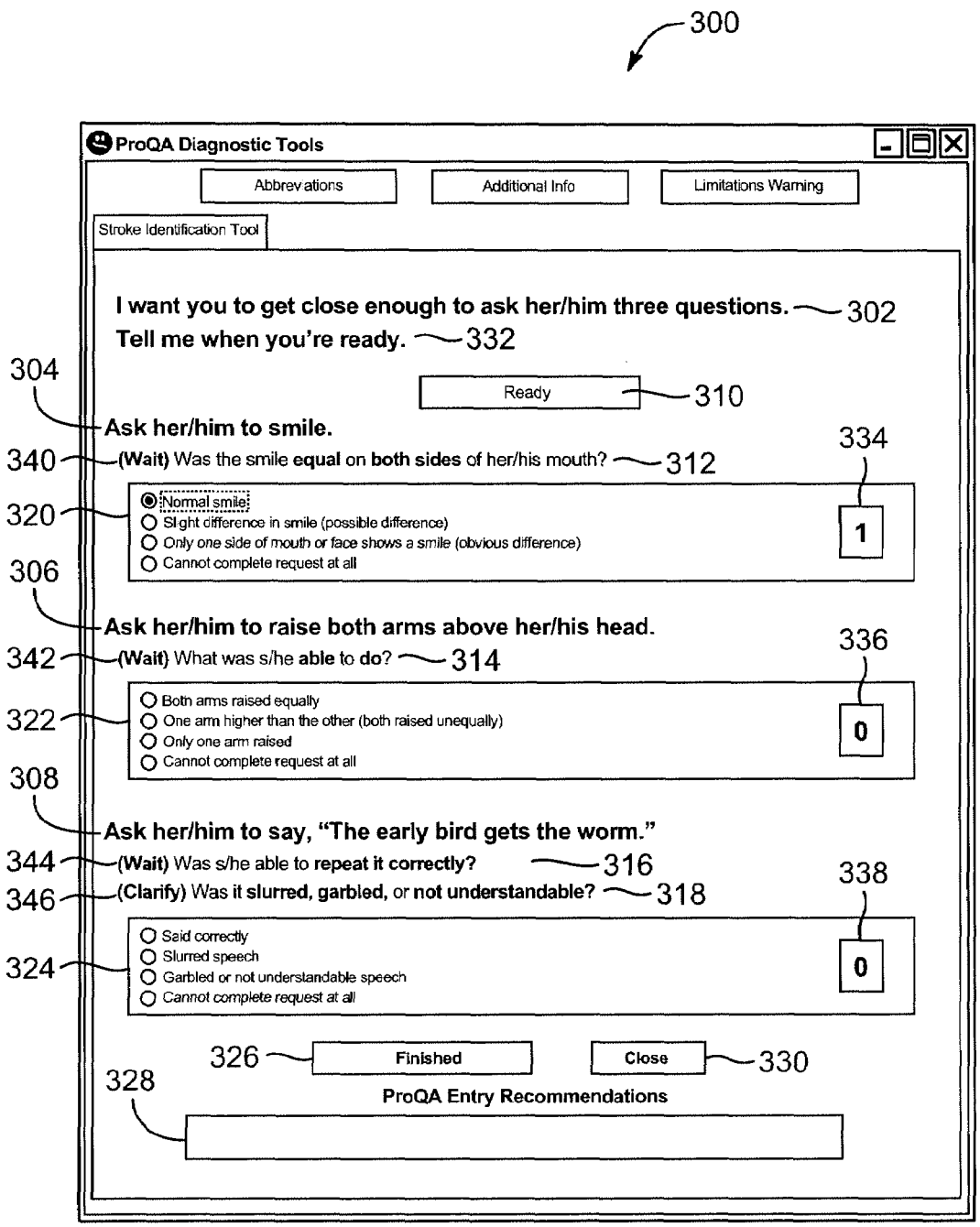

FIG. 3C illustrates the user interface 300 after a first scripted interaction is complete, and after the dispatcher has provided input using the input field 320 of user interface 300. Previously, the dispatcher may have relayed to the caller the diagnostic instruction 304, "Ask her/him to smile," the dispatcher may have waited in accordance with the interaction instruction 340, and then asked the caller the question 312, "Was the smile equal on both sides of his/her mouth?" As shown in FIG. 3C, the caller may have responded to the question, relaying back to dispatcher over the telephone that, "Yes, the patient's smile was equal on both sides," and the dispatcher utilized the input field 320 to input that the patient's smile was a "Normal smile." As shown in FIG. 3C, the dispatcher has clicked the radio button of the input field 320 that corresponds to "Normal smile."

The user interface 300 may further provide an answer field 334 to provide quick indication to the dispatcher the input provided to input field 320. For example, the answer field may provide an answer number to indicate which potential patient response selected in the input field 320 by the dispatcher. For example, if the first potential response of input field 320 is selected, the answer field 334 may present the number "1," and if the second potential response of input field 320 is selected, the answer field 334 may present the number "2," and so on and so forth. The answer number provided in the answer field 334 provides the dispatcher with a quick indication of potential patient response selected in the input field 320. The answer number is more readily identifiable and distinguishable than the selection of the radio button, which reduces inadvertent and/or erroneous input.

As shown in FIG. 3C, answer field 334 provides a "1" to indicate that the dispatcher has selected the first potential response "Normal smile" to diagnostic instruction 304 as provided by the caller's answer to question 312. By contrast, in FIG. 3D the dispatcher has changed the input field 320 to indicate that the patient responded with a "Slight difference in smile (possible difference)," and the answer field 334 provides a "2" to indicate the second potential response was selected.

In another embodiment, the answer fields 334, 336, 338 provide a score to indicate to the dispatcher the importance of a particular caller observation of a patient response as it relates to diagnosing a stroke. The score presented indicates how significantly a patient's response to the diagnostic instruction may indicate that the patient has potentially suffered a stroke. The diagnostic tool may calculate the score or otherwise determine the appropriate score for a given patient response. In the depicted embodiment, a low score provided in the score field 334 may indicate that the patient's response suggests that the patient has not suffered a stroke, or that there is low probability that the patient has suffered a stroke, whereas a high score provided in the score field may indicate that the patient's response suggests a high likelihood that the patient has suffered a stroke. A range of scores may be possible to indicate varying degrees of likelihood that the patient's response suggests that the patient may have suffered a stroke. For example, a score of "1" may indicate that the patient's response suggests a low probability that the patient has suffered a stroke, a score of "2" may indicate a slightly higher probability, a score of "3" may indicate a moderately higher probability, and a score of "4" may indicate that the patient's response suggests a high probability that the patient may have suffered a stroke.

Figure 3D:
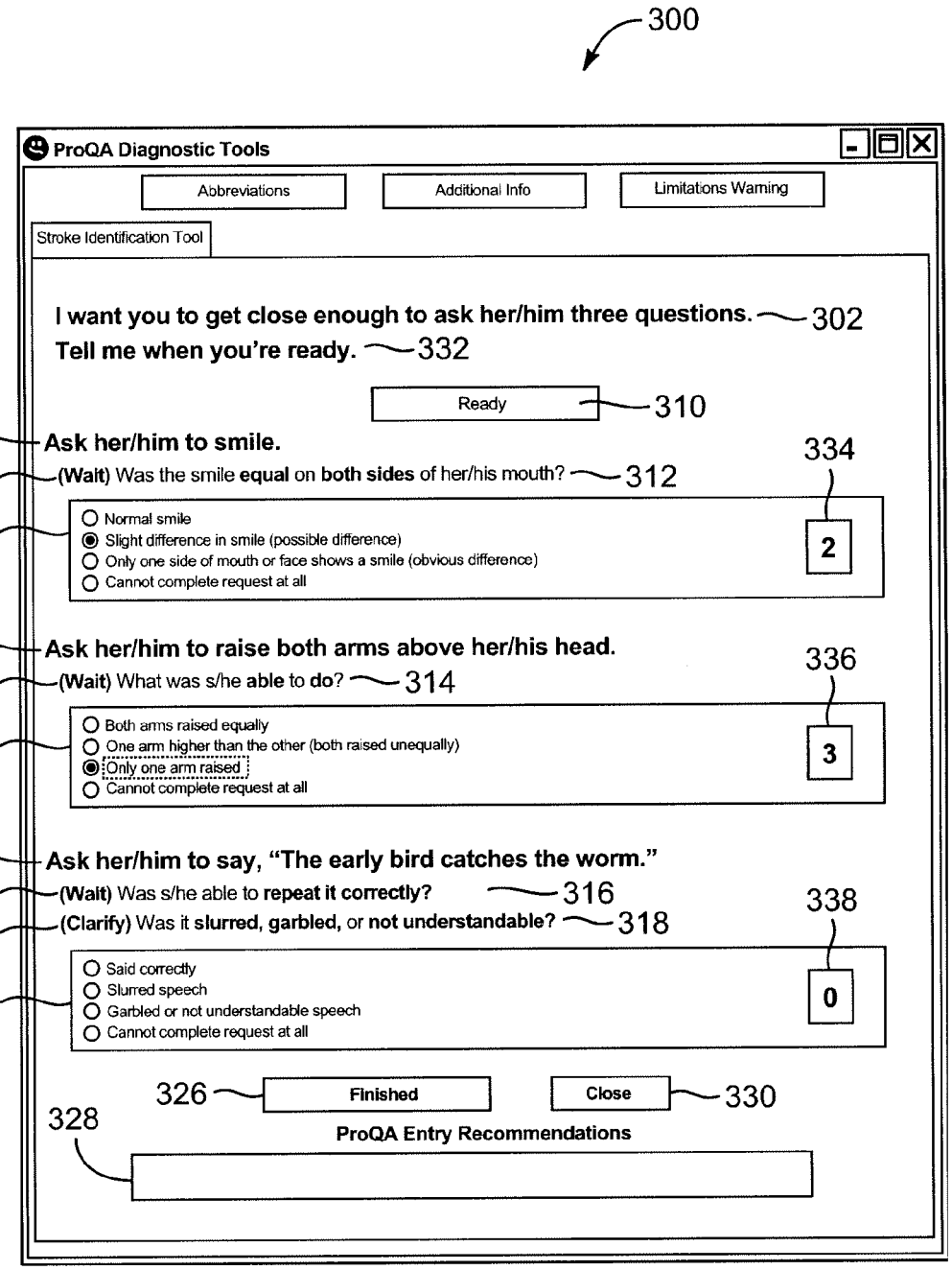

As an illustrative example, consider answer field 334 in FIG. 3C, which provides a "1" as a result of a dispatcher inputting that a patient provided a "Normal smile" in response to diagnostic instruction 304. A score of "1" may suggest a low likelihood that that the patient has suffered a stroke. Similarly, FIG. 3D illustrates that the dispatcher has changed the input field 320 to input that the patient responded with a "Slight difference in smile (possible difference)," and the answer field 334 provides a "2." A score of "2" may indicate the response suggests a slightly higher probability that the patient may have suffered a stroke.

As can be appreciated, other ranges of numbers may be provided as scores in the score field 334. In another embodiment, the scores provided may be inversely proportional to the probability that the patient has suffered a stroke, such that a high score indicates a low probability of stroke and a low score indicates a high probability that the patient has suffered a stroke. In still another embodiment, the scores may be separated by an increment larger or smaller than 1. For example, fractional values are possible, or step from "1" to "3" may indicate increasing probability. Moreover, the increments separating the different scores may vary such that there is not a predictable or consistent increase (e.g., 1, 2.2, 3.8, 6).

In still another embodiment, the level of importance of a patient response may be indicated in the answer field 334 by a visual indicator such as a color, a meter, or a bar graph. For example, the patient response "Normal smile" may be indicated in the answer field 334 by a color such as black, to indicate that such response suggests a low probability that the patient may have suffered a stroke. The patient response "Slight difference in smile (possible difference)" may be indicated in the answer field 334 by a color such as blue, to indicate a slightly higher probability that the patient may have suffered a stroke. The patient response "Only once side of mouth or face shows a smile (obvious difference)" may be indicated in the answer field 334 by a color such as orange, to indicate a moderately higher probability that the patient may have suffered a stroke. The patient response "Cannot complete the request at all" may be indicated in the answer field 334 by a color such as blue, indicate a slightly higher probability that the patient may have suffered a stroke. Other colors may be used to show further increasing probability that a patient response suggests that the patient may have suffered a stroke.

Referring again to the embodiment of FIG. 3C, after the dispatcher has utilized the input field 320 to input the caller's response to the question 312, the user interface 300 may provide the dispatcher a second scripted interaction, including a second diagnostic instruction 306 that the dispatcher can relay to the caller. For example, the user interface 300 may provide a second instruction 306 such as "Ask her/him to raise both arms above her/his head." This second diagnostic instruction 306 may guide the caller in a manner that facilitates identifying a sign or symptom that can be used to diagnose whether the patient may have suffered a stroke. For example, the second diagnostic instruction may guide the dispatcher in further assessing whether the patient may be experiencing any numbness or weakness as may commonly accompany a stroke. When the dispatcher relays this second diagnostic instruction 306 to the caller, the caller is guided to ask the patient to raise her/his arms above her/his head.

A second interaction instruction 342, such as "Wait," may be provided to guide the dispatcher in interacting with the caller by prompting the dispatcher to allow the caller time to perform the instruction and observe the patient's response. The second interaction instruction 342 may be provided in parentheses, to distinguish from instructions intended to be relayed to the caller, and thereby indicate that the interaction instruction 342 is intended solely for the dispatcher.

The user interface 300 further provides a second question 314 for the dispatcher to ask the caller to aid the caller in assessing the patient's response to the second diagnostic instruction 306. The dispatcher can ask the caller the second question 314 to gather information about the caller's observations of the patient's response. The information gathered may be information concerning a potential sign or symptom of a stroke. For example, the second question 314 provided by the user interface 300 may be "Was s/he able to do it?" (i.e., was the patient able to raise her/his arms above her/his head?), guiding the caller to identify whether the patient has suffered any numbness or weakness commonly occurring with stroke victims.

A second input field 322 may be provided by the user interface 300 to enable the dispatcher to provide to the stroke identification tool an input that is indicative of the caller's response to the second question 314. The second input field 322 may provide a way for the dispatcher to enter the caller's observations of the patient's response to the second diagnostic instruction 306 as communicated in the caller's response to the second question 314. The second input field 322 is provided by user interface 300 as a group of radio buttons, similar to the input field 320. The second input field 322 in the depicted embodiment may have four radio buttons, and each radio button may have an associated label providing a potential response of the caller, such as "Both arms raised equally," "One arm raised higher than the other (both raised unequally), "Only one arm raised," and "Cannot complete request at all." The potential responses may correlate with a potential sign or symptom that the patient may have suffered a stroke. For example, the patient's inability to raise both arms equally can indicate that the patient may have suffered a stroke.

FIG. 3D illustrates the user interface 300 after the second scripted interaction is complete, after the dispatcher has provided input using the second input field 322. (Also, as previously described with reference to FIG. 3C, the dispatcher may have changed the input of the input field 320 and, accordingly, input field 320 as shown in FIG. 3D does not correspond to FIG. 3C.) Previously, the dispatcher may have provided the caller the second instruction 306 and asked the caller the second question 314. The caller may have responded to the second question 314, relaying back to the dispatcher over the telephone, that the patient was only able to raise one arm above her/his head. Accordingly, as shown in FIG. 3D, the dispatcher has clicked the radio button of the second input field 322 that corresponds to the potential patient response "Only one arm raised." A answer field 336 provides an answer number "3," indicating that the dispatcher has input the third potential patient response.

After the dispatcher has utilized the second input field 322 to input the caller's response to the second question 314, the user interface 300 provides the dispatcher a third scripted interaction, having a third diagnostic instruction 308 that the dispatcher can relay to the caller. The third diagnostic instruction may further guide the caller in a manner that facilitates determining whether the patient may have suffered a stroke. For example, the user interface 300 may provide a third instruction 308 such as "Ask her/him to say, 'The early bird catches the worm.'" Stroke victims often exhibit slurred speech, or even speech that is garbled or cannot be understood, and the third diagnostic instruction guides the caller in identifying this sign or symptom.

A third interaction instruction 344, such as "Wait," may be provided in parentheses to guide the dispatcher in interacting with the caller by prompting the dispatcher to allow the caller time to perform the instruction and observe the patient's response. The user interface 300 may also provide a third question 316 for the dispatcher to ask the caller to aid the caller in assessing the patent's response to the third diagnostic instruction 308. For example, the third question 316 provided by the user interface 300 may be "Was s/he able to repeat it correctly?" (i.e., was the patient able to correctly say "The early bird catches the worm").

The user interface 300 may also provide a fourth interaction instruction 346, such as "Clarify," to prompt the dispatcher to ask an additional question to clarify the caller's observations of the patient's response to the third diagnostic instruction 308. The fourth interaction instruction 346 may be provided in parentheses to distinguish it as an interaction instruction intended solely for the dispatcher, and not to be relayed to the caller. The user interface 300 further provides a fourth question 318 for the dispatcher to ask the caller to clarify the caller's observations of the patient's response to the third diagnostic instruction 308. For example, in the depicted embodiment, the user interface 300 may provide the fourth question 318, "Was it slurred, garbled, or not understandable?" Thus, the fourth question 318 clarifies whether the patient's response to the third diagnostic instruction 308 exhibited slurred or garbled speech, as commonly occurs with stroke victims.

The user interface 300 may also provide a third input field 324 by which the dispatcher can provide to the stroke identification tool an input that is indicative of the caller's response to the second question 314. The third input field 324 may provide a way for the dispatcher to enter the caller's observations of the patient's response to the third diagnostic instruction 308 as communicated in the caller's responses to the third question 316 and fourth question 318. The third input field 324 may be provided by user interface 300 as a group of radio buttons. The third input field 324 may be provided as four radio buttons, and each of the radio buttons may have an associated label providing a potential response of the caller, such as "Said correctly," "Slurred speech," "Garbled or not understandable speech," and "Cannot complete request at all." These potential responses may correlate with a potential sign or symptom that the patient may have suffered a stroke.

Figure 3E:
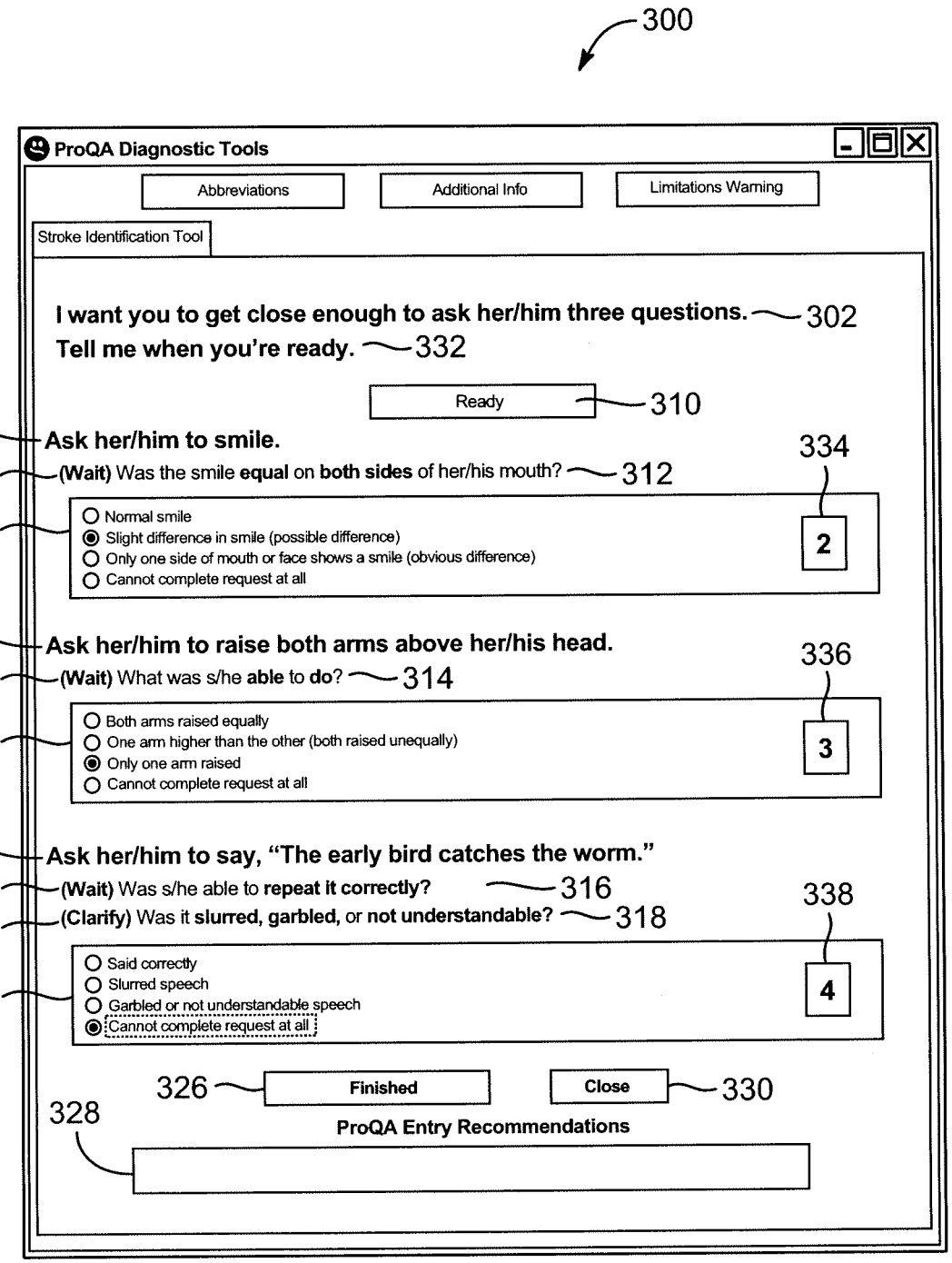

FIG. 3E is the user interface 300 after the third scripted interaction is complete, after the dispatcher has provided input using the third input field 324. The dispatcher may have previously provided the third diagnostic instruction 308 to the caller and the caller may have responded to the third question 316 and fourth question 318, relaying back to the dispatcher over the telephone, that the patient was not able to complete the request at all. Accordingly, as shown in FIG. 3E, the dispatcher has clicked the radio button of the third input field 324 that corresponds to the potential patient response "Cannot complete request at all." A third answer field 338 provides an answer number "4," indicating that the fourth potential patient response on input field 324 was selected by the dispatcher.

After the dispatcher has completed all the scripted interactions, providing input into all the input fields 320, 322, 324, the user interface 300 may provide a finished input 326 that can be clicked to complete and/or terminate the diagnostic function of the stroke identification tool. The finished input 326 may be provided as a button. The dispatcher can click on the finished input 326 button to indicate to the diagnostic tool that the dispatcher has completed relaying the diagnostic instructions and inputting the information concerning the patient's responses as gathered by the questions. The finished input 326 may, when clicked, also signal to the diagnostic tool to process the input and provide a determination or recommendation as to whether the patient may have suffered a stroke. If the dispatcher changes the input provided to an input field 320, 322, 324, the dispatcher may again click the finished input 326 to cause stroke identification tool to again process the input and provide a determination or recommendation as to whether the patient may have suffered a stroke. Still further, clicking the finished input 326 may also signal to the diagnostic tool to communicate the input received via input fields 320, 322, 324 to the emergency medical dispatch protocol and/or determinant value calculator. As shown by the illustrated embodiment, the user interface 300 may present the finished input 326 by automatically pre-selecting it, such that the dispatcher could, for example, press enter to finish (in lieu of clicking the finished input 326). In another embodiment, the finished input 326 may be inactive until appropriate input has been provided to the input fields 320, 322, 324.

Figure 3F:
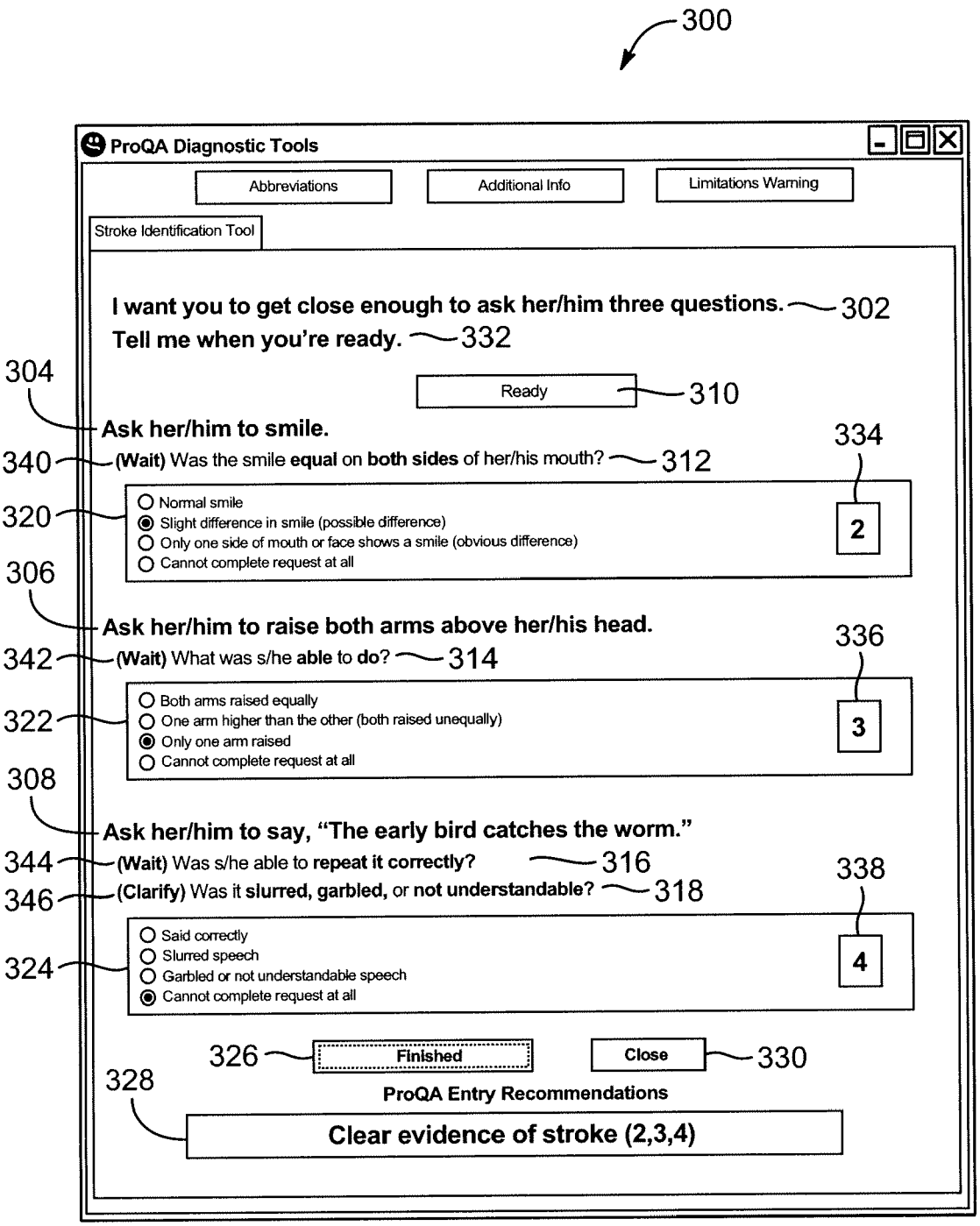

FIG. 3F is the user interface 300 after the dispatcher has provided input using the finished input 326. The stroke identification tool processes the input provided via the input fields 320, 322, 324 and generates a recommendation to display in the recommendation field 328. FIGS. 5A-5F illustrate a flow diagram for generating a recommendation, according to one embodiment. The recommendation may be an indication of the probability that the patient has suffered a stroke. The recommendation may also comprise additional instructions and/or a suggested course of action for the dispatcher and/or the caller.

In the depicted embodiment, the diagnostic tool processes the input associated with "Slight difference in smile (possible difference)," "Only one arm raised," and "Cannot complete request at all," to generate a recommendation that there is "Clear evidence of a stroke (2,3,4)." The answer numbers "(2,3,4)" are also included to provide the dispatcher a quick indication of the precise combination of question answers (i.e. the patient responses) that were selected and used in the determination of the recommendation. The recommendation is presented to the dispatcher to provide indication of the processing (or analysis) of the diagnostic tool. The diagnostic tool makes the determination whether the patient has likely suffered a stroke. The dispatcher is relieved of performing any diagnostic functions, and does not need to have any medical training or experience to provide a consistent reliable response to the scenario as communicated by the emergency caller.

In another embodiment, the diagnostic tool may process scores generated for displaying in each answer field, having pre-processed the input to generate each score. Alternatively, the diagnostic tool may process the input separately and distinctly from generating the scores. The recommendation may include the results of the stroke identification tool determination as to whether the patient may have suffered a stroke.

The recommendation and/or information provided concerning the patient's responses to the diagnostic instructions can also be communicated to the emergency medical dispatch protocol 108 and/or determinant value calculator 110 of the emergency medical dispatch system 100 (see FIG. 1). The recommendation and/or information may be utilized by the emergency medical dispatch protocol 108 and/or determinant value calculator 110 to generate an appropriate emergency medical response and/or determinant value that can be transmitted to emergency responders. The recommendation and/or information may also be used by the emergency medical dispatch system 100 to establish a priority for the call.

A close input 330 is also provided to by the user interface 300 to close the diagnostic tool and/or diagnostic tool interface 300. In the depicted embodiment, the close input 330 is provided as a button that the user can click on. The dispatcher clicks the close input 330 button to close the stroke identification tool. In another embodiment, the close input 330 may also signal to the diagnostic tool to transfer the recommendation and/or the information provided concerning the patient's diagnostic instruction responses to the emergency medical dispatch protocol and/or determinant value calculator, prior to the diagnostic tool closing.

The depicted embodiment has three sets of scripted interactions (each scripted interaction having, for example, at least one diagnostic instruction, at least one interaction instruction, at least one question concerning the patient's response to the diagnostic instruction, and at least one input field). Although three scripted interactions are provided, other arrangements and configurations are possible. As will be appreciated, in another embodiment more scripted interactions (or fewer scripted interactions) may be provided. In still another embodiment, a scripted interaction may have a varying number of diagnostic instructions, interaction instructions, and questions (as evidenced by the third scripted interaction). Moreover, although the scripted interactions of the depicted embodiment also have an answer field and/or an interaction instruction, other embodiments may provide scripted interactions without these elements.

As can also be appreciated, the order of the scripted interactions may vary. For example, the second scripted interaction including instruction 306, question 342, and input field 322 may be presented before the first scripted interaction (i.e. instruction 304, question 340, and input field 320). Moreover, as can also be appreciated, a dispatcher may proceed through the scripted interactions in any order. Although the presentation of the scripted interactions implies an order, the dispatcher can address each scripted interaction in any order. For example, the dispatcher may address the third scripted interaction first. The third scripted interaction depicted in FIGS. 3A-3F including an instruction 308 such as "Ask her/him to say, 'The early bird gets the worm,'" a question 316 such as "Was s/he able to repeat it correctly?," and a question 318 such as "Was it slurred, garbled, or not understandable?" The dispatcher may choose to address this third scripted interaction prior to addressing the first scripted interaction. Similarly, the dispatcher may choose to address the third scripted interaction after the first scripted interaction and prior to the second scripted interaction. Similarly, the dispatcher may choose to address the second scripted interaction prior to the third scripted interaction.

Furthermore, the embodiment of FIGS. 3A-3F presents all the scripted interactions together, on a single screen of user interface 300 of the stroke identification tool. However, as can be appreciated by a person of ordinary skill, the scripted interactions may be presented on separate screens, providing a definite ordering that the scripted interactions should be addressed. Still further, the instruction and question of each scripted interaction may also be presented on separate screens.

Figure 4:
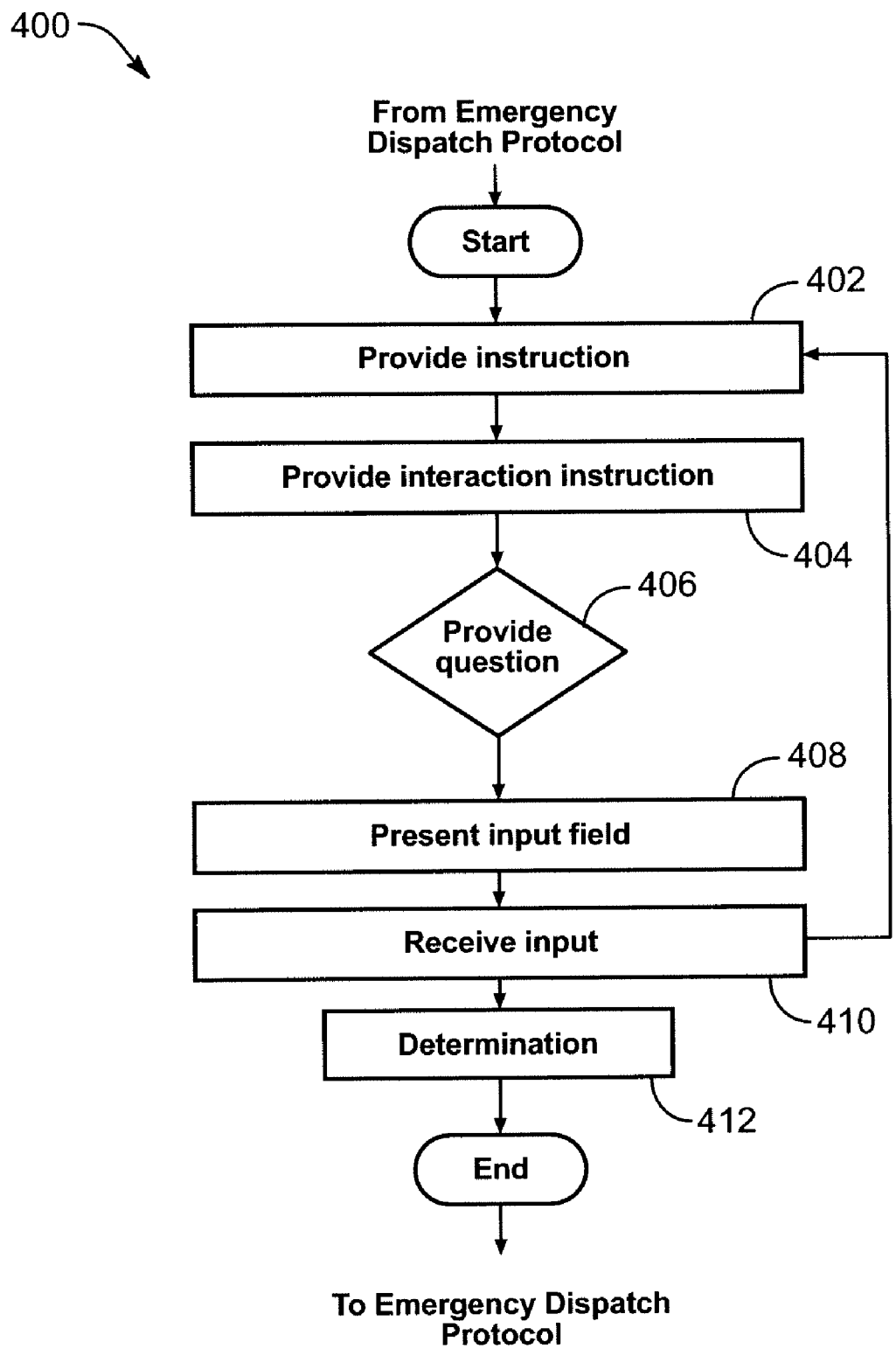
FIG. 4 is a flow diagram of a protocol of a stroke identification tool providing instructions and questions to a dispatcher.

FIG. 4 is a flow diagram of a scripted interaction presented by a protocol 400 of a stroke identification tool, according to one embodiment. The stroke identification tool is launched from within the emergency dispatch protocol. The emergency dispatch protocol may automatically launch the tool based on input received by the emergency dispatch protocol indicating that the patient may have suffered a stroke. The stroke identification tool may also be launched manually, as desired, by the dispatcher. When the stroke identification tool is launched, the logic flow passes from the emergency dispatch protocol to the logic flow of the stroke identification tool as illustrated in the flow diagram of the stroke identification tool protocol 400.

The protocol 400 provides 402 an instruction that a dispatcher can relay to the caller. The protocol 400 may also provide 404 an interaction instruction to direct the dispatcher in interacting with the caller. The protocol then provides 406 a question to facilitate the caller obtaining and relaying information about the patient's response to the instruction. The protocol 400 also presents 408 an input field to enable the dispatcher to provide the protocol with input corresponding to the patient response to the instruction and the protocol receives 410 the dispatcher-entered input. The protocol may then provide additional scripted interactions, jumping back to the step providing 402 an instruction. Alternatively, the protocol 400 may make a determination 412 as to whether the patient has likely suffered a stroke based on the input received 410. After the determination 412 is made, the logic flow of the protocol 400 ends and control is transferred back to the emergency dispatch protocol.

Figure 5:
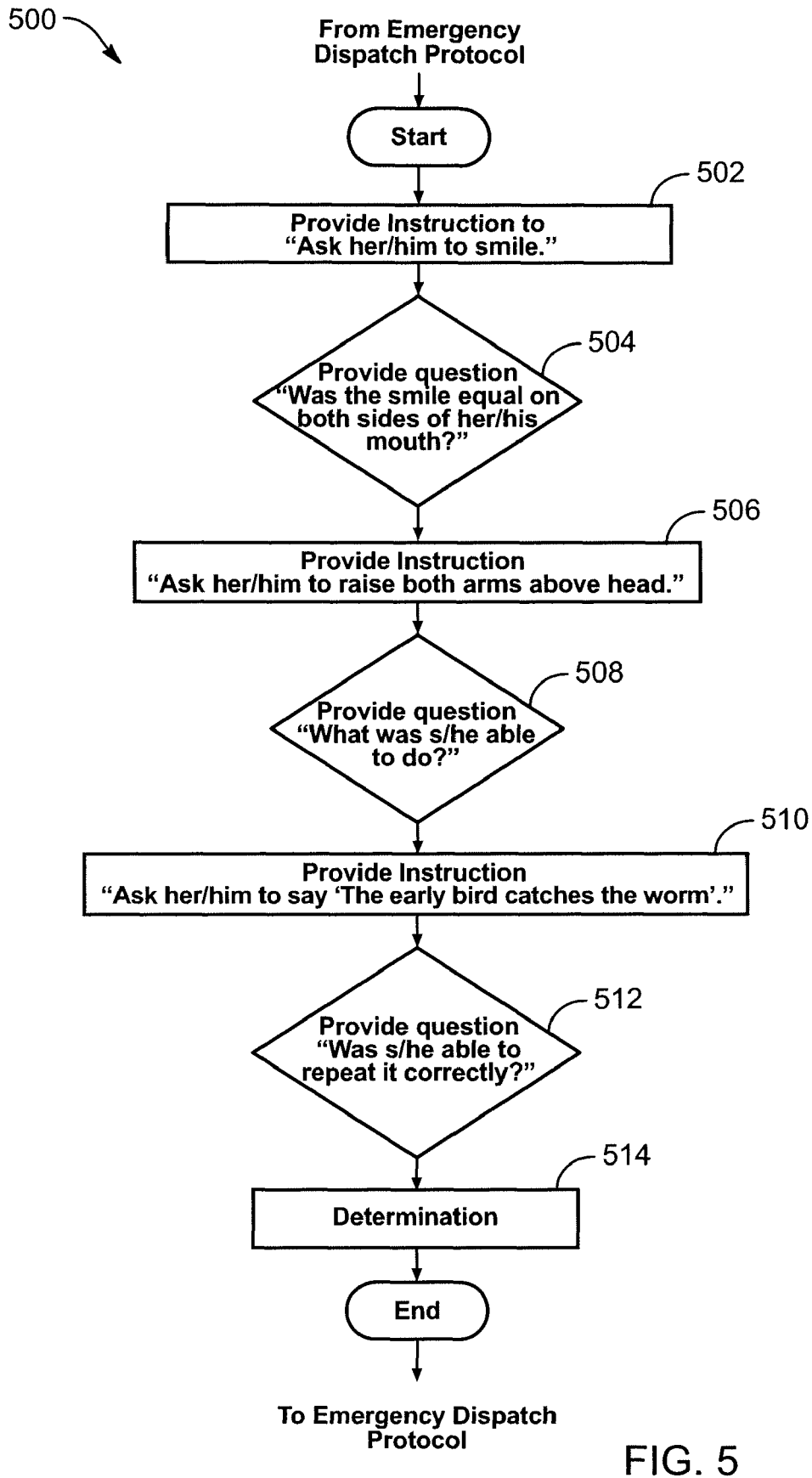
FIG. 5 is a flow diagram of a particular protocol 500 of a stroke identification tool.

FIG. 5 is a flow diagram of a particular protocol 500 of a stroke identification tool providing instructions and questions to a dispatcher, according to one embodiment. As previously explained, the stroke identification tool protocol may present a series of scripted interactions comprising an instruction and a question. Although not depicted in FIG. 5, protocol 500 may include additional steps, such as providing an interaction instruction, presenting an input field, and receiving input, as illustrated by protocol 4 of FIG. 4.

In the embodiment of FIG. 5, the protocol 500 of the stroke identification tool provides 502 a first instruction such as "Ask her/him to smile." The protocol 500 then provides 504 a first question, such as "Was the smile equal on both sides of her/his mouth?" to obtain information about the patient's response to the first instruction. The protocol then provides 506 a second instruction such as "Ask her/him to raise both arms above her/his head" and provides 508 a second question such as "What was s/he able to do?" The protocol then provides 510 a third instruction such as "Ask her/him to say 'The early bird catches the worm'" and provides 512 a third question such as "Was s/he able to repeat it correctly?"

In conjunction with providing questions 504, 508, 512, the protocol 500 also provides input fields as depicted in FIGS. 3A-3F and 4, and described with reference to the same. The input fields enable a dispatcher to provide input corresponding to the caller's answer to the question communicating the patient's response to the instruction. The protocol 500 receives the input for making a determination 514 as to whether the patient has likely suffered a stroke. The determination 516 is based on the input provided by the dispatcher, as discussed in greater detail below with reference to FIGS. 6A-6D. The protocol 500 then returns to the emergency dispatch protocol. The results of the determination and/or the dispatcher-entered input may also be returned to the emergency dispatch protocol.

Figure 6A:
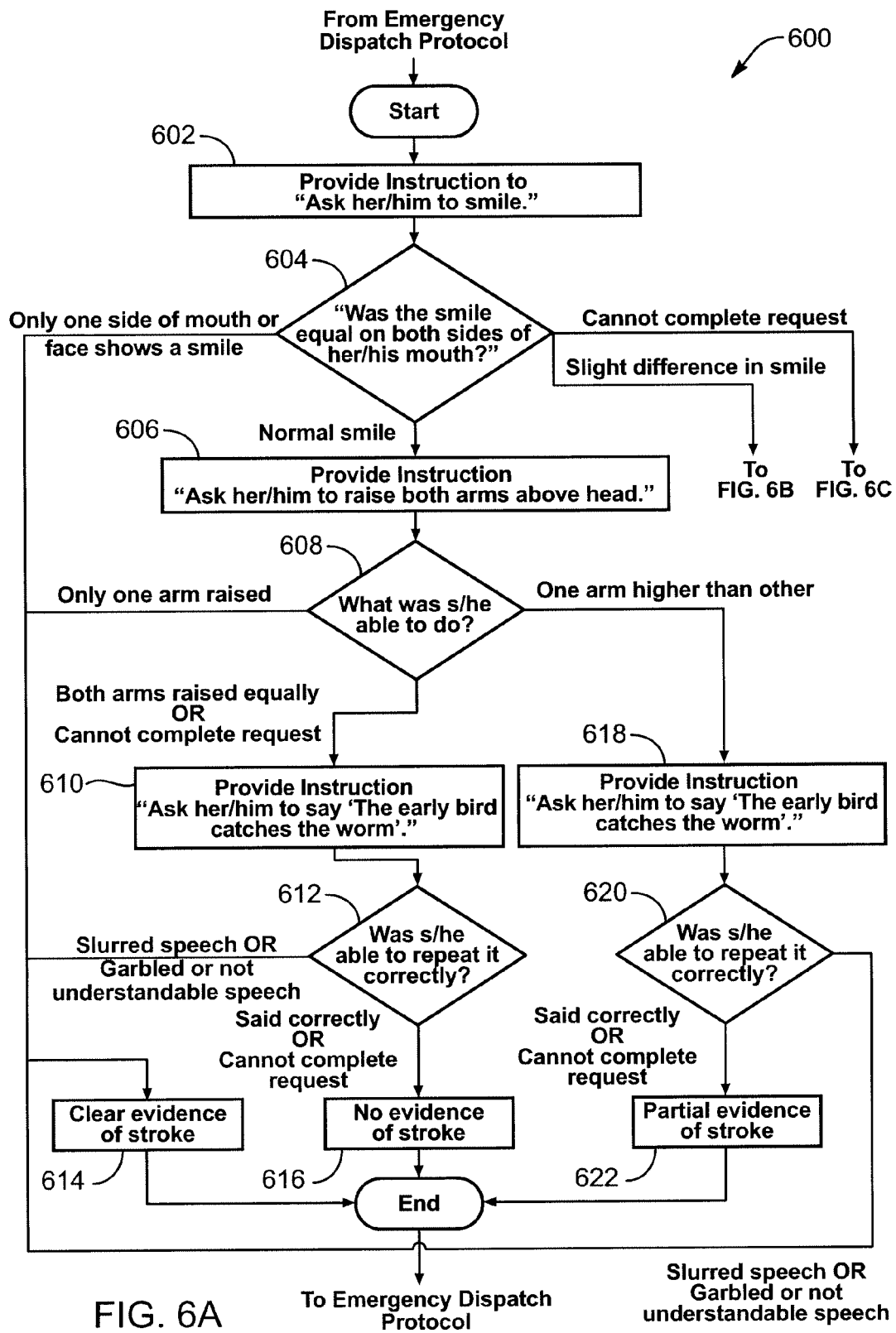
FIGS. 6A-6D are a flow diagram of a stroke identification tool identifying whether a patient has suffered a stroke.
Figure 6B:
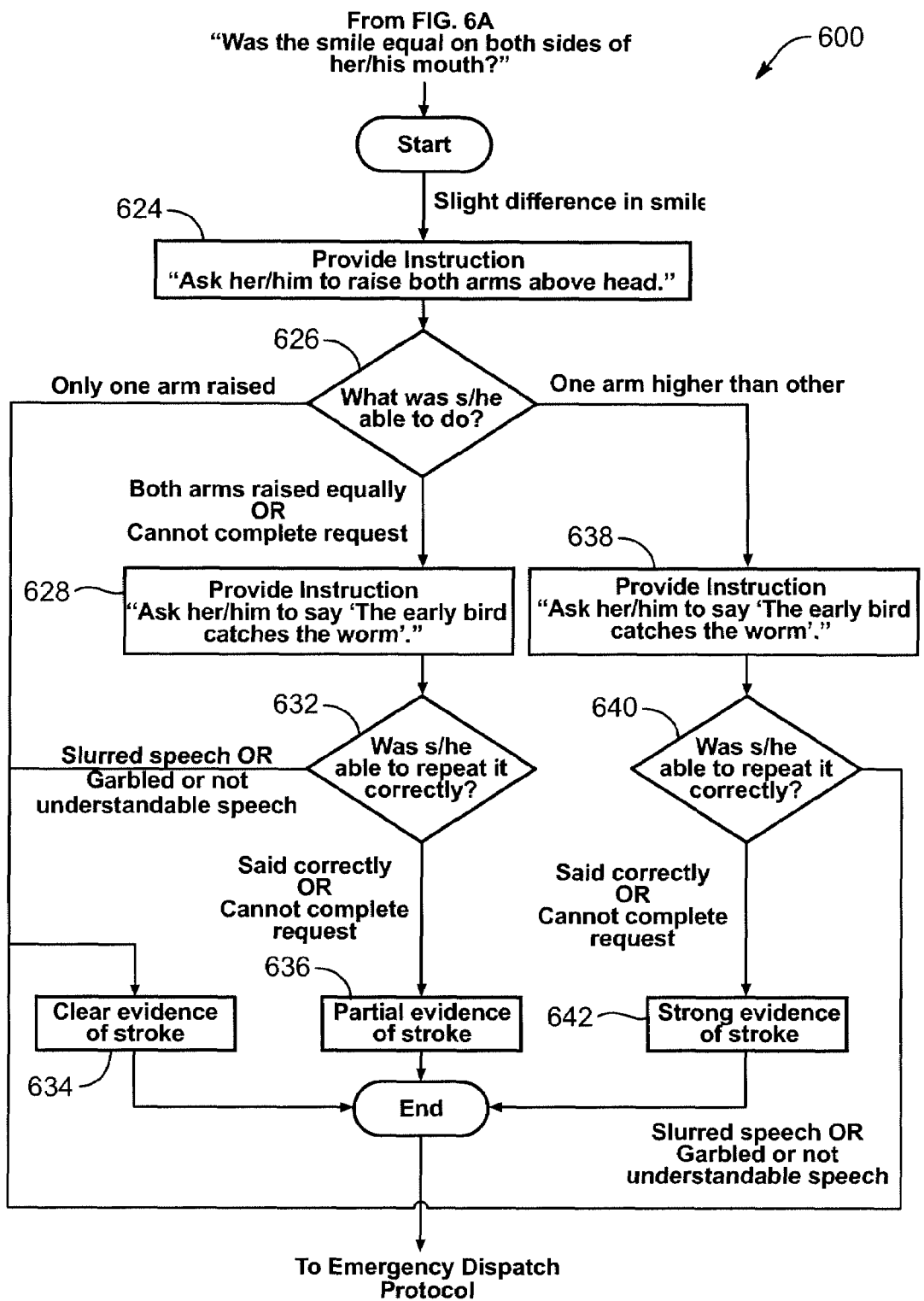
Figure 6C:
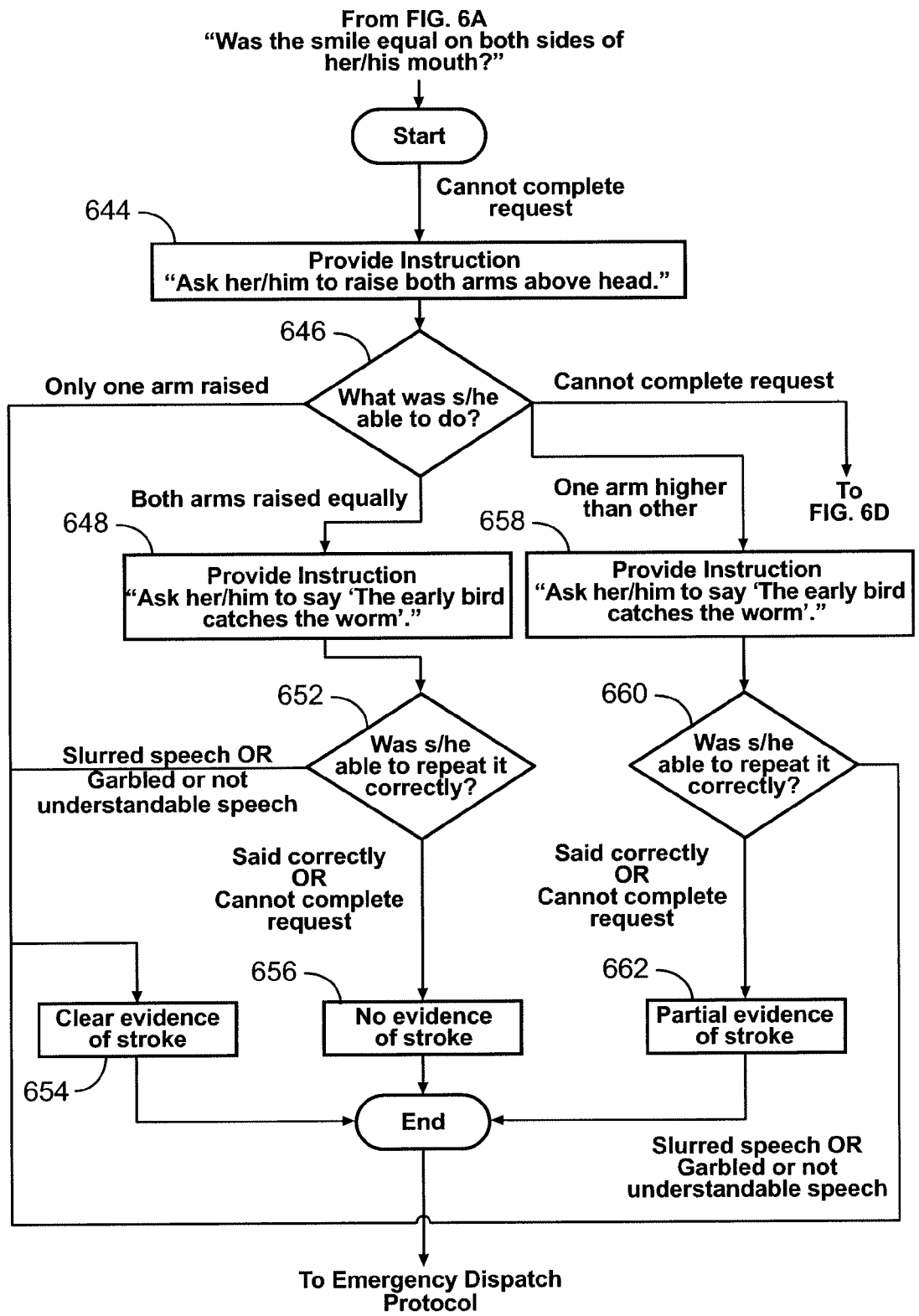

FIGS. 6A-6D are a flow diagram of a protocol 600 of a stroke identification tool determining whether a patient has likely suffered a stroke, according to one embodiment. The logic path to the determination depends on the input provided. In FIGS. 6A-6D, receipt of input is represented as the paths out of the question blocks. Referring specifically to FIG. 6A, after being initiated from within the emergency dispatch protocol, the stroke identification tool protocol 600 provides 602 an instruction such as "Ask her/him to smile." The protocol 600 then provides 604 a first question such as "Was the smile equal on both sides of her/his mouth?" Depending on the input provided (which indicates the caller's response to the question about the patient's response to the instruction), the protocol 600 proceeds along different paths. If the input received indicates "only one side of mouth or face shows a smile," the determination 614 is made that there is clear evidence of a stroke. The logic path of the protocol 600 when the input indicates "Slight difference in smile" is illustrated in FIG. 6B. The logic path of the protocol 600 when the input indicates "Cannot complete request" is shown in FIG. 6C.

If the input indicates "Normal smile," the protocol 600 provides 606 an instruction such as "Ask her/him to raise both arms above head." The protocol 600 provides 608 a second question such as "What was s/he able to do?" to ascertain from the caller the patient's response to the instruction. Again, depending on the input provided in response to that question, the protocol 600 proceeds along different paths. If the input received indicates "Only one arm raised," the determination 614 is made that there is clear evidence of a stroke. If the input received indicates "Both arms raised equally" or the patient "Cannot complete request," the logic flow proceeds along a path that is different than the path when the input received indicates "One arm higher than other."

Regardless of which path the logic flow proceeds along, the protocol 600 provides 610, 618 an instruction such as "Ask her/him to say 'The early bird catches the worm,'" and provides 612, 620 a third question such as "Was s/he able to repeat it correctly?" Moreover, regardless of which path the logic flow proceeds along, if the input received in response to the third question provided 612, 620 indicates "Slurred speech" or "Garbled or not understandable speech," then the determination 614 is made that there is clear evidence of a stroke. However, if the response to the second question provided 608 is "Both arms raised equally" or "Cannot complete request," and the response to the third question provided 612 is "Said correctly" or "Cannot complete the request," then the determination 616 is made that there is no evidence of a stroke. If the response to the second question provided 608 is "One arm higher than other" and the response to the third question provided 620 is "Said correctly" or "Cannot complete the request," then the determination is made that there is partial evidence of a stroke. After the determination 614, 616, 622 is made, the protocol 600 ends and control passes back to the emergency dispatch protocol.

Figure 6D:
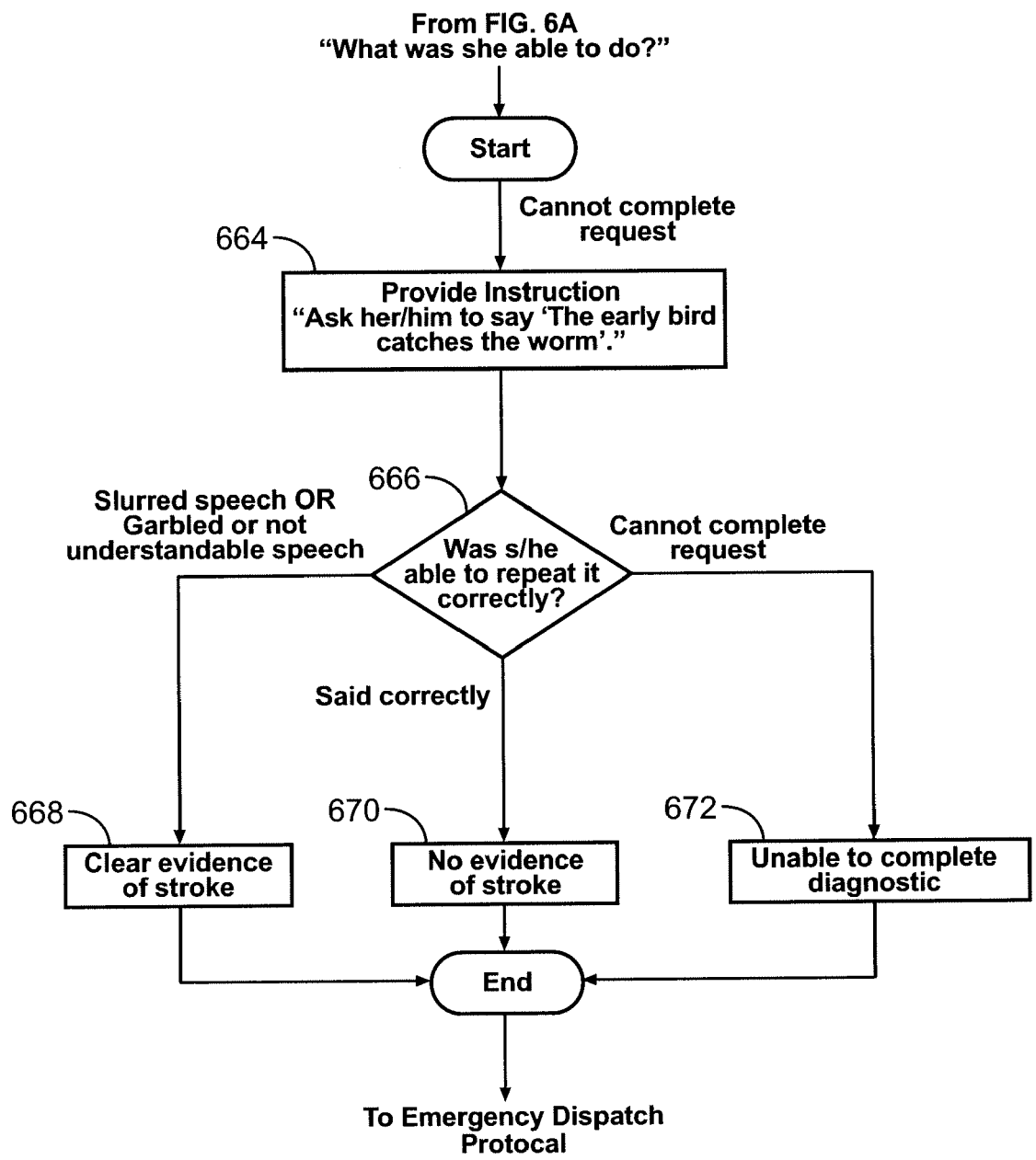

FIG. 6B illustrates the logic flow of the protocol 600 if the input provided in response to the first question indicates "Slight difference in smile." FIG. 6C illustrates the logic flow of the protocol 600 if the input provided in response to the first question indicates "Cannot complete request." FIG. 6D illustrates the logic flow of the protocol 600 if the input provided in response to the second question indicates "Cannot complete request." As illustrated, these alternate branches of the protocol 600 provide 624, 628, 638, 644, 648, 658, 664 instructions and provide 626, 632, 640, 646, 652, 660, 666 questions. The logic flow is somewhat similar to the logic flow of FIG. 6A, except that the input provided in response to the questions may lead to determinations 634, 638, 642, 654, 656, 662, 668, 670, 672 that may be different. For example, the input provided may suggest "No evidence of a stroke," "Partial evidence of a stroke," "Strong evidence of a stroke," "Clear evidence of a stroke," or "Unable to complete diagnostic."

The logic paths of protocol 600 as shown in FIGS. 6A-6D illustrate the that some responses may be clear evidence of a stroke, where as other responses alone may be merely partial evidence or strong evidence of a stroke. For example, the input "Only one side of mouth shows a smile," "Only one arm raised," "Slurred speech," and "Garbled or not understandable speech" may lead to a determination "Clear evidence of stroke." By contrast, the input "Slight difference in smile," or "One arm higher than the other" may lead to a determination "Partial evidence of stroke" or "Strong evidence of stroke." As can be appreciated, the input provided (and implicitly the patient responses) may vary and may change in importance in the determination as additional research and information is gained regarding the signs and symptoms of a stroke. The illustrated logic paths of protocol 600 demonstrate how input may be internally weighted differently and then processed to generate a determination whether a patient has likely suffered a stroke.

The embodiments described above, as previously explained, end and transfer control to the emergency dispatch protocol (or otherwise allow the emergency dispatch protocol to resume). As can be appreciated, the embodiments may transfer or otherwise communicate the determination or recommendation as to whether the patient may have suffered a stroke and/or the input received via input fields to the emergency dispatch protocol and/or the determinant value calculator, and may aid in determining the priority of the dispatch response. The result of the determination may be incorporated into the traversal of the logic tree of the emergency dispatch protocol. For example, subsequent determinations as to how the emergency dispatch protocol proceeds along the logic tree may be based, at least in part, upon the determination of the stroke identification tool. A person of ordinary skill can appreciate that the recommendation and input may be communicated to other components of the emergency medical dispatch system 100 as well. Moreover, other information may be communicated as well. All information taken by the tools may be stored by the system 100 and conveyed to the determinant value calculator 110, the reporting module 114, the CAD system 112 and/or to trained emergency responders. This information may be used to assist emergency responders prior to arrival. The diagnostic tools 120, including the stroke identification tool 122, greatly improve information collection and intervention for emergency medical response situations and will be an aid in saving lives.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer-implemented method to assist a dispatcher when communicating with a caller via telephone regarding a medical emergency of a patient, comprising:

a dispatch center computer system providing an emergency dispatch protocol to assist the dispatcher, the protocol presenting a plurality of pre-scripted interrogatories for the dispatcher to ask the caller to gather information regarding the emergency and generate an emergency dispatch response emergency responders;

the dispatch center computer system initiating a diagnostic tool on the dispatch center computer, the diagnostic tool configured to assist the dispatcher in guiding the caller to obtain information that can be used by the diagnostic tool to diagnose whether the patient has suffered a stroke;

the diagnostic tool presenting to the dispatcher a user interface;

the diagnostic tool providing an instruction via the user interface for the dispatcher to vocally relay to the caller over the telephone to assist the caller in identifying signs and symptoms that the patient has likely suffered a stroke;

the diagnostic tool receiving dispatcher-entered input indicative of caller-relayed information concerning the caller's observations of a response of the patient, including signs and symptoms that indicate whether the patient has suffered a stroke, wherein the caller's observations are vocally relayed over the telephone to the dispatcher; and the diagnostic tool determining the likelihood that the patient has suffered a stroke based on the dispatcher-entered input indicative of the caller-relayed information.

2. The computer-implemented method of claim 1, further comprising the diagnostic tool indicating to the dispatcher, via the user interface, the results of the determination whether the patient has suffered a stroke.

3. The computer-implemented method of claim 1, further comprising:
the diagnostic tool generating a recommendation that can be relayed to the emergency responders based on the determination whether the patient has suffered a stroke; and
the user interface of the diagnostic tool displaying the recommendation to the dispatcher.

4. The computer-implemented method of claim 1, wherein the dispatch center computer system initiates the diagnostic tool based on dispatcher-entered input indicative of one or more responses of the caller to the interrogatories presented to the dispatcher by the protocol.

5. The computer-implemented method of claim 1, further comprising the dispatch center computer system presenting to the dispatcher an emergency dispatch protocol user interface having a diagnostic tool launch input to initiate the diagnostic tool, wherein the dispatch center computer system initiates the diagnostic tool in response to the diagnostic tool launch input.

6. The computer-implemented method of claim 1, further comprising the dispatch center computer system determining a priority for the emergency dispatch response based on the diagnostic tool determining whether the patient has suffered a stroke.

7. The computer-implemented method of claim 6, wherein the dispatch center computer system determining the priority further comprises determining a determinant value.

8. The computer-implemented method of claim 1, wherein the diagnostic tool providing instructions via the user interface includes providing instructions that direct the caller to ask the patient to perform an action, and wherein the computer-implemented method further comprises the diagnostic tool providing questions to the dispatcher to direct to the caller regarding the caller's observations of the patient performing the action.

9. The computer-implemented method of claim 8, wherein the diagnostic tool providing instructions that direct the caller to ask the patient to perform an action comprises providing an instruction that directs the caller to ask the patient to smile, and wherein the diagnostic tool providing to the dispatcher questions to direct to the caller regarding the caller's observations comprises asking the caller if the patient's smile was equal on both sides of the patient's mouth.

10. The computer-implemented method of claim 8, wherein the diagnostic tool providing instructions that direct the caller to ask the patient to perform an action comprises providing an instruction that directs the caller to ask the patient to raise both arms above the patient's head, and wherein the diagnostic tool providing to the dispatcher questions to direct to the caller regarding the caller's observations comprises asking the caller if the patient was able to raise both arms above the patient's head.

11. The computer-implemented method of claim 8, wherein the diagnostic tool providing instructions that direct the caller to ask the patient to perform an action comprises providing an instruction that directs the caller to ask the patient to say a phrase, and wherein the diagnostic tool providing to the dispatcher questions to direct to the caller regarding the caller's observations comprises asking the caller if the patient was able to repeat the phrase correctly.

12. The computer-implemented method of claim 1, further comprising the diagnostic tool providing input fields via the user interface by which the dispatcher can enter input indicative of caller-relayed information concerning the caller's observations of signs and symptoms of a stroke.

13. The computer-implemented method of claim 12, wherein the input fields comprise radio buttons associated with potential caller observations.

14. The computer-implemented method of claim 12, further comprising the diagnostic tool indicating to the dispatcher, via the user interface, an answer number corresponding to dispatcher-entered input indicative of the caller observation.

15. The computer implemented method of claim 1, further comprising the diagnostic tool providing a finished input via the user interface, wherein the diagnostic tool makes the determination whether the patient has suffered a stroke in response to the finished input.

16. The computer implemented method of claim 1, further comprising:
the user interface of the diagnostic tool providing a close input; and
the diagnostic tool terminating operation in response to the close input.

17. The computer implemented method of claim 1, further comprising the diagnostic tool providing to the emergency dispatch protocol the results of the diagnostic tool determination whether the patient has suffered a stroke.

18. The computer implemented method of claim 1, wherein the emergency dispatch protocol comprises an emergency medical dispatch protocol.

19. A computer readable storage medium including computer readable instruction code for performing a method to assist a dispatcher when communicating with a caller via telephone regarding a medical emergency of a patient, the method comprising:
providing an emergency dispatch protocol to assist the dispatcher, the protocol presenting a plurality of pre-scripted interrogatories for the dispatcher to ask the caller to gather information regarding the emergency and generate an emergency dispatch response;
initiating a diagnostic tool on a dispatch center computer, the diagnostic tool configured to assist the dispatcher in guiding the caller to obtain information that can be used by the diagnostic tool to diagnose whether the patient has suffered a stroke;
the diagnostic tool presenting to the dispatcher a user interface;
the diagnostic tool providing instructions via the user interface for the dispatcher to vocally relay to the caller over the telephone to assist the caller in identifying signs and symptoms that the patient has likely suffered a stroke;
the diagnostic tool receiving dispatcher-entered input indicative of caller-relayed information concerning the caller's observations of signs and symptoms that indicate whether the patient has suffered a stroke, wherein the caller's observations are vocally relayed over the telephone to the dispatcher; and
the diagnostic tool determining whether the patient has likely suffered a stroke based on the dispatcher-entered input indicative of the caller-relayed information.

20. The computer readable storage medium of claim 19, further comprising the diagnostic tool indicating to the dispatcher, via the user interface, the results of the determination whether the patient has suffered a stroke.

21. The computer readable storage medium of claim 19, wherein the diagnostic tool is initiated based on dispatcher-entered input indicative of one or more responses of the caller to the interrogatories presented to the dispatcher by the emergency dispatch protocol.

22. The computer-readable storage medium of claim 19, wherein the method further comprises presenting to the dispatcher an emergency dispatch protocol user interface having a diagnostic tool launch input to initiate the diagnostic tool, wherein the diagnostic tool is initiated in response to the diagnostic tool launch input.

23. The computer-readable storage medium of claim 19, wherein the method further comprises determining a priority for the emergency dispatch response based on the diagnostic tool determining that the patient has suffered a stroke.

24. The computer-readable storage medium of claim 19, wherein the method further comprises the diagnostic tool providing input fields via the user interface by which the dispatcher can enter input indicative of caller-relayed information concerning the caller's observations of signs and symptoms of a stroke.

25. A computer system to perform a method to assist a dispatcher when communicating with a caller via telephone regarding a medical emergency of a patient, the computer system comprising:
   a processor;
   an input device in electrical communication with the processor;
   an output device in electrical communication with the processor; and
   a memory in electrical communication with the processor, and having stored thereon:
   an emergency dispatch protocol including a plurality of pre-scripted interrogatories for a dispatcher to ask a caller to generate an emergency dispatch response; and
   a diagnostic tool to assist the dispatcher in guiding the caller to obtain information that can be used by the diagnostic tool to diagnose whether the patient has suffered a stroke, wherein the diagnostic tool is configured to:
   present to the dispatcher a user interface on the output device, including instructions for the dispatcher to vocally relay to the caller over the telephone to assist the caller in identifying signs and symptoms that the patient has suffered a stroke;
   receive dispatcher-entered input indicative of caller-relayed information concerning the caller's observations of signs and symptoms that suggest the patient has likely suffered a stroke, wherein the caller's observations are vocally relayed over the telephone to the dispatcher; and
   determine whether the patient has likely suffered a stroke based on the dispatcher-entered input indicative of the caller-relayed information.

26. The computer system of claim 25, wherein the diagnostic tool is further configured to indicate to the dispatcher the results of determining whether the patient has likely suffered a stroke.

27. The computer system of claim 25, wherein the diagnostic tool is further configured to provide to the emergency dispatch protocol the results of determining whether the patient has suffered a stroke.

28. The computer system of claim 25, further comprising a determinant value calculator stored on the memory to calculate a determinant value to prioritize an emergency response, wherein the diagnostic tool is configured to provide to the determinant value calculator the results of determining whether the patient has suffered a stroke.

29. The computer system of claim 25, further comprising a reporting module stored on the memory to measure the performance of a dispatcher, wherein the diagnostic tool is configured to provide to the reporting module the results of determining whether the patient has suffered a stroke.

* * * * *

UNITED STATES PATENT AND TRADEMARK OFFICE
CERTIFICATE OF CORRECTION

PATENT NO. : 8,355,483 B2
APPLICATION NO. : 12/558045
DATED : January 15, 2013
INVENTOR(S) : Jeffrey J. Clawson It is certified that error appears in the above-identified patent and that said Letters Patent is hereby corrected as shown below:

In the Specifications

Column 17, line 39, please replace "638" with "636".

Signed and Sealed this
Twenty-fifth Day of June, 2013

Teresa Stanek Rea
*Acting Director of the United States Patent and Trademark Office*